United States Patent
Agarwal et al.

(10) Patent No.: US 7,217,726 B2
(45) Date of Patent: May 15, 2007

(54) ANTIBACTERIAL AGENTS

(75) Inventors: Shiv Kumar Agarwal, Chennai (IN); Mrinal Kanti Guha, Chennai (IN); Surendrakumar Satyanarayan Pandey, Chennai (IN); Matte Marianna Samuel, Chennai (IN)

(73) Assignee: Orchid Chemicals & Pharmaceuticals Limited, Chennai (IN)

( * ) Notice: Subject to any disclaimer, the term of this patent is extended or adjusted under 35 U.S.C. 154(b) by 450 days.

(21) Appl. No.: 10/469,648

(22) PCT Filed: Aug. 21, 2003

(86) PCT No.: PCT/IB03/03459

§ 371 (c)(1),
(2), (4) Date: Sep. 3, 2003

(87) PCT Pub. No.: WO2004/018439

PCT Pub. Date: Mar. 4, 2004

(65) Prior Publication Data

US 2005/0070526 A1    Mar. 31, 2005

(30) Foreign Application Priority Data

Aug. 22, 2002   (IN)   .................. 618/MAS/2002

(51) Int. Cl.
*C07D 413/10*   (2006.01)
*A61K 31/422*   (2006.01)

(52) U.S. Cl. .................. 514/376; 544/60; 548/232; 540/544; 549/232

(58) Field of Classification Search .................. 544/60; 548/232; 514/376; 540/544; 549/232
See application file for complete search history.

(56) References Cited

U.S. PATENT DOCUMENTS

| 5,547,950 | A | 8/1996 | Hutchinson et al. |
| 6,342,513 | B1 | 1/2002 | Hester, Jr. et al. |
| 2002/0137754 | A1 | 9/2002 | Hester, Jr. |

FOREIGN PATENT DOCUMENTS

WO    WO 02/06278 A1    1/2002

*Primary Examiner*—James O. Wilson
*Assistant Examiner*—Paul V. Ward
(74) *Attorney, Agent, or Firm*—Oliff & Berridge, PLC

(57) ABSTRACT

The present invention provides novel compounds of the general formula (I), their derivatives, their analogs, their tautomeric forms, their stereoisomers, their polymorphs, their hydrates, their solvates, their pharmaceutically acceptable salts and pharmaceutically acceptable compositions containing them. The present invention more particularly provides novel oxazolidinone derivatives of the general formula (I)

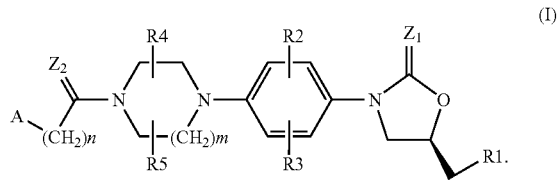

17 Claims, No Drawings

ANTIBACTERIAL AGENTS

FIELD OF THE INVENTION

The present invention provides novel compounds of the general formula (I), their derivatives, their analogs, their tautomeric forms, their stereoisomers, their polymorphs, their hydrates, their solvates, their pharmaceutically acceptable salts and pharmaceutically acceptable compositions containing them. The present invention more particularly provides novel oxazolidinone derivatives of the general formula (I).

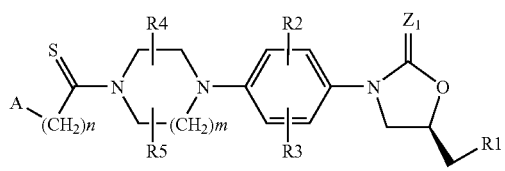

(I)

The present invention also provides a process for the preparation of the above said novel oxazolidinone derivatives of the formula (I) their derivatives, their analogs, their tautomeric forms, their stereoisomers, their polymorphs, their hydrates, their solvates, their pharmaceutically acceptable salts, and pharmaceutical compositions containing them.

The novel oxazolidinone derivatives of the present invention may be useful as antibacterial agents and hence are useful in the treatment of conditions such as nosocomial pneumoniae, community acquired pneumoniae, vancomycin resistance enterococci (VRE) caused by methicillin resistance staphylococcus aureus (MRSA) and penicillin resistance streptococcus pneumnoniae. The compounds of the present invention are effective against a number of human or animal pathogens, clinical isolates, including Vancomycin resistant organisms, methicillin resistant organisms.

BACKGROUND OF INVENTION

Several oxazolidinone derivatives have been reported in the literature some of which are relevant are given here:

U.S. Pat. No. 5,547,950 discloses and claims compounds of formula (IIa)

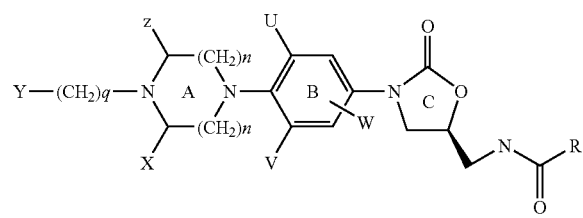

(IIa)

or pharmaceutically acceptable salts there of wherein each n is independently 1 to 3; Y is selected from a-n as defined in the patent; U, V and W are independently $(C_1-C_6)$allyl, fluoro, chloro, bromo, hydrogen or a $(C_1-C_6)$alkyl substituted with one or more of fluoro, chloro, bromo or iodo, preferably U and V are fluoro and W is hydrogen; R is hydrogen, $(C_1-C_{12})$alkyl, $(C_3-C_{12})$cycloalkyl, $(C_1-C_6)$alkoxy, $(C_1-C_6)$alkyl substituted with one or more of fluoro, chloro, bromo, iodo or hydroxy and q is 0 to 4 inclusive.

WO 02/06278 describes a series of oxazolidinone derivatives useful as antimicrobial agents, of the formula (IIb)

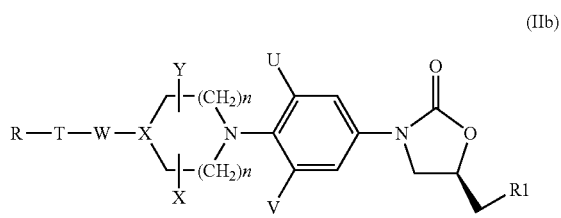

(IIb)

wherein T is a five to seven membered heterocyclic ring, aryl, substituted aryl; R is a substituent on T; X is $CH_2$, CH—S, CH—O and N; Y and Z are independently selected from hydrogen, alkyl, cycloalkyl; U and C are independently selected from alkyl, halogen; W is selected from group $CH_2$, CO, $CH_2NH$, $CH_2NHCH_2$, S, $CH_2CO$ etc; $R^1$ is selected from —NH(C=O)$R^2$, wherein $R^2$ is hydrogen alkyl, cycloalkyl, alkoxy and the like.

U.S. publication No. 2002/0137754 describes a series of oxazolidinone derivatives useful as antimicrobial agents of the formula (IIc)

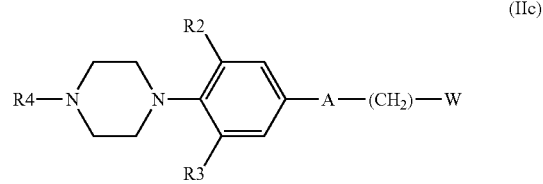

(IIc)

wherein A represents oxazolidinone ring and the like; W is NHC(=S)$R^1$, or —Y-het; Y is NH, O, or S; $R^1$ is H, $NH_2$, $NHC_{1-4}$alkyl, $C_{1-4}$alkenyl, etc; $R^2$ and $R^3$ are independently H, F, Cl or $C_{1-2}$alkyl; $R^4$ is (a) —C(=O)—$CR^5R^6$—O—$R^7$, (b) —C(=O)—$CH_2S(O)$n-$CH_3$, (c) —C(=O)—$CH_2$—S(=O)(=N$R^8$)$CH_3$, (d) —C(=S)—$R^9$, etc; $R^5$ is H; $R^6$ is phenyl, benzyl, etc, $R^7$ is H, $CH_3$ or $C_{1-4}$ alkanoyl; $R^8$ is H, $C_{1-4}$ alkyl, $C_{1-4}$ alkanoyl, —C(=O)NH—$C_{1-4}$ alkyl or —$CO_2C_{1-4}$ alkyl; $R^9$ is $C_{1-4}$alkyl, $CH_2OR_{11}$, S—$C_{1-4}$ alkyl, $OC_{1-4}$ alkyl, or $NR^{12}R^{13}$; $R^{11}$ is H, phenyl, benzyl, $CH_3$ etc; $R^{12}$ and $R^{13}$ are independently H or $C_{1-3}$ alkyl; or $R^{12}$ and $R^{13}$ taken together form a 5- or 6- membered saturated heterocycle, wherein said saturated heterocycle may farther contain one or two additional hetero-atoms selected from a group consisting of O, S(O)$_n$ or $NR^7$; n is 0, 1 or 2; and m is 0 or 1.

U.S. Pat. No. 6,342,513 and WO 00/32599 discloses compounds of the formula (IIc)

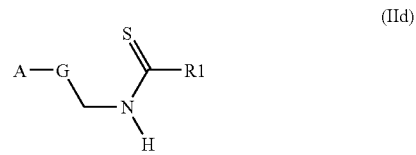

(IId)

wherein G represents oxazolidinone ring and the like; $R^1$ is H, $NH_2$, NH alkyl, alkyl, alkoxy, etc, A is

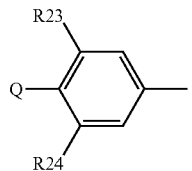

wherein $R^{23}$ and $R^{24}$ represents H, halogen and the like; Q is

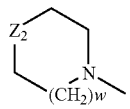

etc., wherein $Z_2$ is $SO_2$—, —O—, —$(NR^{107})$—OS—, —S—, and the like; $R^{107}$ is —$R^{108}$CO— etc, $R^{108}$ is H, alkyl, aryl etc.

OBJECTIVE OF THE INVENTION

We have focused our research to identify novel oxazolidinone derivatives, which are effective against resistant organisms. Our sustained efforts have resulted in novel oxazolidinone derivatives of the formula (I). The novel oxazolidinone derivatives of the present invention may be useful as antibacterial agents and hence are useful in the treatment of conditions such as nosocomial pneumoniae, community acquired pneumoniae, vancomycin resistance enterococci (VRE) caused by methicillin resistance staphylococcus aureus (MRSA) and penicillin resistance streptococcus pneumoniae. The compounds of the present invention are effective against a number of human or animal pathogens, clinical isolates, including Vancomycin resistant organisms, methicillin resistant organisms

SUMMARY OF THE INVENTION

The present invention relates to novel oxazolidinone derivatives of the formula (I)

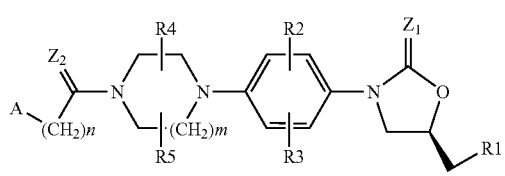

their derivatives, their analogs, their tautomeric forms, their stereoisomers, their polymorphs, their pharmaceutically acceptable salts, wherein $Z^1$ and $Z^2$ may be same or different and represent O or S; $R^1$ represents halogen, azido, nitro, cyano; $XR^6$, where X represents O or S, $R^6$ represents hydrogen, formyl, substituted or unsubstituted groups selected from $(C_1-C_6)$alkyl, cycloalkyl, aryl, aralkyl, acyl, thioacyl, heterocyclyl, heteroaryl, alkylsulfonyl, arylsulfonyl, aralkylsulfonyl; $N(R^{7a}R^{7b})$ where $R^{7a}$ and $R^{7b}$ may be same or different and independently represent hydrogen, formyl, substituted or unsubstituted groups selected from $(C_1-C_6)$alkyl, aryl, aralkyl, heteroaryl, heteroaralkyl or an aminoacid residue which is attached through acid moiety, or $R^{7a}$ and $R^{7b}$ together with nitrogen may represent a mono or bicyclic saturated or unsaturated ring system which may contain one or more heteroatoms selected from O, S or N; or of the formula —NHC(=Y)$R^8$ wherein Y represents O or S, $R^8$ is hydrogen, substituted or unsubstituted groups selected from $(C_1-C_6)$alkyl, $(C_1-C_6)$alkoxy, aryl, $(C_3-C_6)$ cycloalkyl, amino, monoalkylamino, dialkylamino, cycloalkylamino, arylamino, aroylamino, alkylcarbonylamino, arylcarbonylamino, heteroaryl, heterocyclyl, heteroaralkyl, heteroaroylamino, or $R^1$ is of the formula —NHS$(O)_p(C_1-C_4)$alkyl, —NHS$(O)_p(C_1-C_4)$aryl or —NHS$(O)_p(C_1-C_4)$heteroaryl, where p is 0 to 2; $R^2$ and $R^3$ may be same or different and independently represent hydrogen, halogen, hydroxy, alkyl, alkoxy; $R^4$ and $R^5$ may be same or different and independently represent hydrogen, cyano, nitro, amino, halogen, hydroxyl, substituted or unsubstituted groups selected from $(C_1-C_6)$alkyl, haloalkyl, $(C_1-C_6)$alkoxy, $(C_1-C_6)$alkylthio, $(C_3-C_6)$cycloalkyl or either of $R^4$ or $R^5$ represent an oxo or thiooxo group; n is 0, 1 or 2; when $Z^2$ represents S, A represents a $NHR^9$ or substituted or unsubstituted cycloalkyl, aryl, five to seven membered heteroaryl, heterocyclyl wherein the heterocycle is attached through carbon atom, heteroarylalkenyl, heterocyclylalkenyl; wherein $R^9$ represents hydrogen or substituted or unsubstituted group selected from alkyl, aryl, alkoxy, alkenyl, cycloalkyl, heteroaryl or heterocyclyl group; when $Z^2$ represents O, A represents $NHR^9$, where $R^9$ represents phenyl substituted by nitro; substituted or unsubstituted groups selected from alkoxy, alkenyl, cycloalkyl, heteroaryl or heterocyclyl group; m is an integer in the range of 0 to 2; n is an integer ranging from 0–4, with a proviso that when n is 0, $R^9$ does not represent hydrogen or alkyl.

DETAILED DESCRIPTION OF THE INVENTION

Suitable groups represented by $R^1$ may be selected from halogen atom such as fluorine, chlorine, bromine or iodine; azido, nitro, cyano, $XR^6$, $N(R^{7a}R^{7b})$, —NHC(=Y)$R^5$; —NHS$(O)_p(C_1-C_4)$alkyl, —NHS$(O)_p(C_1-C_4)$aryl or —NHS$(O)_p(C_1-C_4)$heteroaryl.

Suitable groups represented by $R^2$ and $R^3$ are selected from hydrogen, halogen atom such as fluorine, chlorine, bromine or iodine; hydroxyl, $(C_1-C_6)$alkyl group such as methyl, ethyl, n-propyl, isopropyl, n-butyl, isobutyl, t-butyl, n-pentyl, isopentyl, hexyl and the like; $(C_1-C_6)$alkoxy group, such as methoxy, ethoxy, n-propoxy, isopropoxy and the like.

Suitable groups represented by $R^4$ and $R^5$ are selected from hydrogen, cyano, nitro, amino, halogen, hydroxyl, $(C_1-C_6)$alkyl group such as methyl, ethyl, n-propyl, isopropyl, n-butyl, isobutyl, t-butyl, n-pentyl, isopentyl, hexyl and the like; haloalkyl such as chloromethyl, chloroethyl, trifluoromethyl, trifluoroethyl, dichloromethyl, dichloroethyl and the like; $(C_1-C_6)$alkoxy group, such as methoxy, ethoxy, n-propoxy, isopropoxy and the like; $(C_1-C_6)$alkylthio group such as methylthio, ethylthio, n-propylthio, iso-propylthio and the like; $(C_3-C_6)$cycloalkyl group such as cyclopropyl, cyclobutyl, cyclopentyl, cyclohexyl and the like or either of $R^4$ or $R^5$ represent an oxo or thiooxo group.

Suitable groups represented by $R^6$ are selected from hydrogen, formyl, substituted or unsubstituted linear or branched $(C_1-C_6)$alkyl group such as methyl, ethyl, n-propyl, isopropyl, n-butyl, isobutyl, t-butyl, n-pentyl, isopentyl, hexyl and the like; ($C_3$–$C_6$)cycloalkyl group such as cyclopropyl, cyclobutyl, cyclopentyl, cyclohexyl and the like, which may be substituted; aryl group such as phenyl, naphthyl and the like, the aryl group may be substituted; aralkyl group such as phenylmethyl, phenylethyl, naphthylmethyl, naphthylethyl and the like, the aralkyl group may be substituted; acyl group such as —C(=O)$CH_3$, —C(=O)$C_2H_5$, —C(=O)$C_3H_7$, —C(=O)$C_6H_{13}$, benzoyl and the like, the acyl group may be substituted; thioacyl group such as —C(=S)$CH_3$, —C(=S)$C_2H_5$, —C(=S)$C_3H_7$, —C(=S)$C_6H_{13}$ and the like, the thioacyl group may be substituted; alkylsulfonyl group such as methylsulfonyl, ethylsulfonyl, n-propylsulfonyl, iso-propylsulfonyl and the like, which may be substituted; arylsulfonyl group such as phenylsulfonyl, naphthylsulfonyl and the like, which may be substituted; aralkylsulfonyl group such as phenylmethylsulfonyl, phenylethylsulfonyl, naphthylmethylsulfonyl, naphthylethylsulfonyl and the like, which may be substituted; heteroaryl group such as pyridyl, thienyl, furyl, pyrrolyl, oxazolyl, thiazolyl, imidazolyl, isooxazolyl, oxadiazolyl, triazolyl, thiadiazolyl, tetrazolyl, pyrimidinyl, pyrazinyl, pyridazinyl, benzopyranyl, benzofuranyl, benzimidazole, benzoxazolyl, benzothiazolyl, benzopyrrolyl, benzoxadiazolyl, benzothiadiazolyl, benzodioxolyl, quinolinyl, dihydroquinolinyl, tetrahydroquinolinyl, isoquinolinyl, dihydroisoquinolinyl, tetrahydroisoquinolinyl and the like, which may be substituted; heterocyclyl group such as pyrrolidinyl, morpholinyl, thiomorpholinyl, piperidinyl, piperazinyl, and the like, which may be substituted.

Suitable groups represented $R^{7a}$ and $R^{7b}$ are selected from hydrogen, formyl, substituted or unsubstituted linear or branched ($C_1$–$C_6$)alkyl group such as methyl, ethyl, n-propyl, isopropyl, n-butyl, isobutyl, t-butyl, n-pentyl, isopentyl, hexyl and the like; aryl group such as phenyl, naphthyl and the like, which may be substituted; aralkyl group such as phenylmethyl, phenylethyl, naphthylmethyl, naphthylethyl and the like, which may be substituted; heteroaryl group such as pyridyl, thienyl, furyl, pyrrolyl, oxazolyl, thiazolyl, imidazolyl, isooxazolyl, oxadiazolyl, triazolyl, thiadiazolyl, tetrazolyl, pyrimidinyl, pyrazinyl, pyridazinyl, benzopyranyl, benzofuranyl, benzimidazolyl, benzoxazolyl, benzothiazolyl, benzopyrrolyl, benzoxadiazolyl, benzothiadiazolyl, benzodioxolyl, quinolinyl, dihydroquinolinyl, tetrahydroquinolinyl, isoquinolinyl, dihydroisoquinolinyl, tetrahydroisoquinolinyl and the like, which may be substituted; heteroaraky group wherein the heteroaryl moiety is as defined above; an aminoacid residue group selected from glycine, alanine, lysine, arginine, asparagine, aspartic acid, cysteine, glutamic acid, glutamine, histidine, iso-leucine, leucine, methionine, phenylalanine, proline, serine, threonine, tryptophan, tyrosine or valine.

Suitable ring systems formed by $R^{7a}$ and $R^{7b}$ together are selected from pyridyl, thienyl, furyl, pyrrolyl, oxazolyl, thiazolyl, imidazolyl, isooxazolyl, oxadiazolyl, triazolyl, thiadiazolyl, tetrazolyl, pyrimidinyl, pyrazinyl, pyridazinyl, benzopyranyl, benzofuranyl, benzimidazolyl, benzoxazolyl, benzothiazolyl, benzopyrrolyl, benzoxadiazolyl, benzothiadiazolyl, benzodioxolyl, quinolinyl, dihydroquinolinyl, tetrahydroquinolinyl, isoquinolinyl, dihydroisoquinolinyl, tetrahydroisoquinolinyl and the like.

Suitable groups represented by $R^8$ are selected from hydrogen, amino, substituted or unsubstituted linear or branched ($C_1$–$C_{10}$)alkyl group such as methyl, ethyl, n-propyl, isopropyl, n-butyl, isobutyl, t-butyl, n-pentyl, isopentyl, hexyl and the like; ($C_1$–$C_{10}$)alkoxy group, such as methoxy, ethoxy, n-propoxy, isopropoxy, butoxy and the like, which may be substituted; aryl group such as phenyl, naphthyl and the like, which may be substituted; ($C_3$–$C_6$)cycloalkyl group such as cyclopropyl, cyclobutyl, cyclopentyl, cyclohexyl and the like, which may be substituted; monoalkylamino group such as $NHCH_3$, $NHC_2H_5$, $NHC_3H_7$, $NHC_6H_{13}$, and the like, which may be substituted; dialkylamino group such as $N(CH_3)_2$, $NCH_3(C_2H_5)$, $N(C_2H_5)_2$ and the like, which may be substituted; arylamino group such as phenylamino or naphthylamino, which may be substituted; alkylcarbonylamino group such as methylcarbonylamino, ethylcarbonylamino, n-propylcarbonylamino, iso-propylcarbonylamino and the like, which may be substituted; arylcarbonylamino group such as phenylcarbonylamino or naphthylcarbonylamino, which may be substituted; heteroaryl group such as pyridyl, thienyl, furyl, pyrrolyl, oxazolyl, thiazolyl, imidazolyl, isooxazolyl, oxadiazolyl, triazolyl, thiadiazolyl, tetrazolyl, pyrimidinyl, pyrazinyl, pyridazinyl, benzopyranyl, benzofuranyl, benzimidazolyl, benzoxazolyl, benzothiazolyl, benzopyrrolyl, benzoxadiazolyl, benzothiadiazolyl, benzodioxolyl, quinolinyl, dihydroquinolinyl, tetrahydroquinolinyl, isoquinolinyl, dihydroisoquinolinyl, tetrahydroisoquinolinyl and the like, which may be substituted; heteroaralkyl group wherein the heteroaryl moiety is as defined above; heterocyclyl group such as pyrrolidinyl, morpholinyl, thiomorpholinyl, piperidinyl, piperazinyl, and the like, which may be substituted; cycloalkyl amino group such as cyclopropyl amino, cyclobutylamino, cyclopentylamino, cyclohexylamino and the like, which may be substituted.

Suitable groups represented by A are selected from substituted or unsubstituted aryl such as phenyl, naphthyl and the like; ($C_3$–$C_6$)cycloalkyl group such as cyclopropyl, cyclobutyl, cyclopentyl, cyclohexyl and the like, which may be substituted; heteroaryl group such as pyridyl, thienyl, furyl, pyrrolyl, oxazolyl, thiazolyl, imidazolyl, isooxazolyl, oxadiazolyl, triazolyl, thiadiazolyl, tetrazolyl, pyrimidinyl, pyrazinyl, pyridazinyl, benzopyranyl, benzofuranyl, benzimidazolyl, benzoxazolyl, benzothiazolyl, benzopyrrolyl, benzoxadiazolyl, benzothiadiazolyl, benzodioxolyl, quinolinyl, dihydroquinolinyl, tetrahydroquinolinyl, isoquinolinyl, dihydroisoquinolinyl, tetrahydroisoquinolinyl and the like, which may be substituted; heterocyclyl group such as pyrrolidinyl, morpholinyl, thiomorpholinyl, piperidinyl, piperazinyl, and the like, the heterocyclyl group may be substituted; heteroaryl ($C_2$–$C_{10}$)alkenyl, wherein the heteroaryl is as defined above, which may be substituted; heterocyclyl ($C_2$–$C_{10}$)alkenyl, wherein the heterocyclyl group is as defined above. The substituents are selected from cyano, nitro, acyl, halogen atom such as fluorine, chlorine, bromine or iodine; amino; substituted or unsubstituted linear or branched ($C_1$–$C_6$)alkyl group such as methyl, ethyl, n-propyl, isopropyl, n-butyl, isobutyl, t-butyl, n-pentyl, isopentyl, hexyl and the like; ($C_2$–$C_{10}$)alkenyl, ($C_1$–$C_6$)alkoxy group, such as methoxy, ethoxy, n-propoxy, isopropoxy and the like, which may be substituted; ($C_1$–$C_6$)alkylthio group such as methylthio, ethylthio, n-propylthio, iso-propylthio and the like, winch may be substituted; ($C_3$–$C_6$)cycloalkyl group such as cyclopropyl, cyclobutyl, cyclopentyl, cyclohexyl and the like, which may be substituted; thio $C_1$–$C_6$) alkyl, which may be substituted; aryl group such as phenyl, naphthyl and the like, which may be substituted; acyl group such as —C(=O)$CH_3$, —C(=O)$C_2H_5$, —C(=O)$C_3H_7$, —C(=O)$C_6H_{13}$, —C(=S)$CH_3$, —C(=S)$C_2H_5$, —C(=S)$C_3H_7$, —C(=S)$C_6H_{13}$, benzoyl and the like, which may be substituted; acylamino group such as NHC(=O)$CH_3$, NHC(=O)$C_2H_5$, NHC(=O)$C_3H_7$, NHC(=O)$C_6H_{13}$, and the like, which may be substituted; monoalkylamino group such as NHCH$_3$, NHC$_2$H$_5$, NHC$_3$H$_7$, NHC$_6$H$_{13}$, and the like, which may be substituted; dialkylamino group such as N(CH$_3$)$_2$, NCH$_3$(C$_2$H$_5$), N(C$_2$H$_5$)$_2$ and the like, which may be substituted; —CH=NOR$^6$, carboxylic acid or its esters. The substituents are selected from hydroxy, halogen, nitro, cyano or amino.

Suitable group represented by R$^9$ is selected from substituted or unsubstituted linear or branched (C$_2$–C$_{10}$)alkenyl, (C$_1$–C$_6$)alkoxy group, such as methoxy, ethoxy, n-propoxy, isopropoxy and the like, which may be substituted; (C$_3$–C$_6$) cycloalkyl group such as cyclopropyl, cyclobutyl, cyclopentyl, cyclohexyl and the like, which may be substituted; aryl group such as phenyl, naphthyl and the like, which may be substituted; heteroaryl group such as pyridyl, thienyl, furyl, pyrrolyl, oxazolyl, thiazolyl, imidazolyl, isooxazolyl, oxadiazolyl, triazolyl, thiadiazolyl, tetrazolyl, pyrimidinyl, pyrazinyl, pyridazinyl, benzopyranyl, benzofuranyl, benzimidazolyl, benzoxazolyl, benzothiazolyl, benzopyrrolyl, benzoxadiazolyl, benzothiadiazolyl, benzodioxolyl, quinolinyl, dihydroquinolinyl, tetrahydroquinolinyl, isoquinolinyl, dihydroisoquinolinyl, tetrahydroisoquinolinyl and the like, which may be substituted; heterocyclyl group such as pyrrolidinyl, morpholinyl, thiomorpholinyl, piperidinyl, piperazinyl, and the like, the heterocyclyl group may be substituted.

The substituents on any of the groups represented by R$^1$, R$^4$, R$^5$, R$^6$, R$^{7a}$, R$^{7b}$, R$^8$ and R$^9$ may be selected from halogen, hydroxy, formyl, nitro, cyano, azido, amino, alkyl, aryl, alkylamino, alkylaminocarbonyl, haloalkyl, acylamino, alkoxy, acyl and these substituents are as defined above.

Pharmaceutically acceptable salts of the present invention include alkali metal like Li, Na, and K, alkaline earth metal like Ca and Mg, salts of organic bases such as diethanolamine, α-phenylethylamine, benzylamine, piperidine, morpholine, pyridine, hydroxyethylpyrrolidine, hydroxyethylpiperidine, choline and the like, ammonium or substituted ammonium salts, aluminum salts. Salts also include amino acid salts such as glycine, alanine, cystine, cysteine, lysine, arginine, phenylalanine, guanidine etc. Salts may include acid addition salts where appropriate which are, sulphates, nitrates, phosphates, perchlorates, borates, hydrohalides, acetates, tartrates, maleates, citrates, succinates, palmoates, methanesulphonates, tosylates, benzoates, salicylates, hydroxynaphthoates, benzenesulfonates, ascorbates, glycerophosphates, ketoglutarates and the like. Pharmaceutically acceptable solvates may be hydrates or comprising other solvents of crystallization such as alcohols.

Representative compounds according to the present invention include:

(S)-N-[3-[3-Fluoro-4-[4-(thiophen-3-ylthiocarbonyl)piperazin-1-yl]phenyl]-2-oxooxazolidin-5-ylmethyl]thioacetamide;
(S)-N-[3-[3-Fluoro-4-[4-(quinolin-2-ylthiocarbonyl)piperazin-1-yl]phenyl]-2-oxooxazolidin-5-ylmethyl]thioacetamide;
(S)-N-[3-[3-Fluoro-4-[4-(thiophen-2-ylthiocarbonyl)piperazin-1-yl]phenyl]-2-oxooxazolidin-5-ylmethyl]thioacetamide;
(S)-N-[3-[3-Fluoro-4-[4-(quinolin-3-ylthiocarbonyl)piperazin-1-yl]phenyl]-2-oxooxazolidin-5-ylmethyl]thioacetamide;
(S)-N-[3-[3-Fluoro-4-[4-(5-nitrofuran-2-ylthiocarbonyl) piperazin-1-yl]phenyl]-2-oxooxazolidin-5-ylmethyl]thioacetamide;
(S)-N-[3-[3-Fluoro-4-[4-(cyclopropylthiocarbonyl)piperazin-1-yl]phenyl]-2-oxooxazolidin-5-ylmethyl]thioacetamide;
(S)-N-[3-[3-Fluoro-4-[4-(5-methylthiophen-2-ylthiocarbonyl)piperazin-1-yl]phenyl]-2-oxooxazolidin-5-ylmethyl] thioacetamide;
(S)-N-[3-[3-Fluoro-4-[4-(5-chlorothiophen-2-ylthiocarbonyl)piperazin-1-yl]phenyl]-2-oxooxazolidin-5-ylmethyl] thioacetamide;
(S)-N-[3-[3-Fluoro-4-[4-(3-methylthiophen-2-ylthiocarbonyl)piperazin-1-yl]phenyl]-2-oxooxazolidin-5-ylmethyl] thioacetamide;
(S)-N-[3-[3-Fluoro-4-[4-(2-chloropyridin-3-ylthiocarbonyl) piperazin-1-yl]phenyl]-2-oxooxazolidin-5-ylmethyl]thioacetamide;
(S)-N-[3-[3-Fluoro-4-[4-(3-chlorothiophen-2-ylthiocarbonyl)piperazin-1-yl]phenyl]-2-oxooxazolidin-5-ylmethyl] thioacetamide;
(S)-N-[3-[3-Fluoro-4-[4-(5-bromothiophen-2-ylthiocarbonyl)piperazin-1-yl]phenyl]-2-oxooxazolidin-5-ylmethyl] thioacetamide;
(S)-N-[3-[3-Fluoro-4-[4-(thiophen-2-ylthioacetyl)piperazin-1-yl]phenyl]-2-oxooxazolidin-5-ylmethyl]thioacetamide;
(S)-N-[3-[3-Fluoro-4-[4-(pyrazin-2-ylthiocarbonyl)piperazin-1-yl]phenyl]-2-oxooxazolidin-5-ylmethyl]thioacetamide;
(S)-N-[3-[3-Fluoro-4-[4-(phenylthiocarbonyl)piperazin-1-yl]phenyl]-2-oxooxazolidin-5-ylmethyl]thioacetamide;
(S)-N-[3-[3-Fluoro-4-[4-(6-chloropyridin-3-ylthiocarbonyl) piperazin-1-yl]phenyl]-2-oxooxazolidin-5-ylmethyl]thioacetamide;
(S)-N-[3-[3-Fluoro-4-[4-(3-methylisoxazol-5-ylthiocarbonyl)piperazin-1-yl]phenyl]-2-oxooxazolidin-5-ylmethyl] thioacetamide;
(S)-N-[3-[3-Fluoro-4-[4-(5-methylisoxazol-3-ylthiocarbonyl)piperazin-1-yl]phenyl]-2-oxooxazolidin-5-ylmethyl] thioacetamide;
(S)-N-[3-[3-Fluoro-4-[4-(6-methylpyrazin-3-ylthiocarbonyl)piperazin 1-yl]phenyl]-2-oxooxazolidin-5-ylmethyl] thioacetamide;
(S)-N-[3-[3-Fluoro-4-[4-(cyclobutanethionyl)piperazinyl-1-yl]phenyl]-2-oxooxazolidin-5-ylmethyl]thioacetamide;
(S)-N-[3-[3-Fluoro-4-[4-(cyclopentanethionyl)piperazinyl-1-yl]phenyl]-2-oxooxazolidin-5-ylmethyl]thioacetamide;
(S)-N-[3-[3-Fluoro-4-[4-(imidazol-2-ylthiocarbonyl)piperazin-1-yl]phenyl]-2-oxooxazolidin-5-ylmethyl]thioacetamide;
(S)-N-[3-[3-Fluoro-4-[4-(pyrrolidin-2-ylthiocarbonyl)piperazin-1-yl]phenyl]-2-oxooxazolidin-5-ylmethyl]acetamide;
(S)-N-[3-[3-Fluoro-4-[4-(pyrrolidin-2-ylthiocarbonyl)piperazin-1-yl]phenyl]-2-oxooxazolidin-5-ylmethyl]thioacetamide;
(S)-N-[3-[3-Fluoro-4-[4-(aminothioacetyl)piperazin-1-yl] phenyl]-2-oxooxazolidin-5-ylmethyl]acetamide hydrochloride;
(S)-N-[3-[3-Fluoro-4-[4-(aminothioacetyl)piperazin-1-yl] phenyl]-2-oxooxazolidin-5-ylmethyl]thioacetamide hydrochloride;
(S)-N-[3-[3-Fluoro-4-[4-(5-nitrofuran-3-ylthiocarbonyl) piperazin-1-yl]phenyl]-2-oxooxazolidin-5-ylmethyl]acetamide;
(S)-N-[3-[3-Fluoro-4-[4-(6-methylpyrazin-3-ylthiocarbonyl)piperazin-1-yl]phenyl]-2-oxooxazolidin-5-ylmethyl] acetamide;

(S)-N-[3-[3-Fluoro-4-[4-(pyrazin-2-ylthiocarbonyl)piperazin-1-yl]phenyl]-2-oxooxazolidin-5-ylmethyl]acetamide;
(S)-N-[3-[3-Fluoro-4-(4-(N,N'-dimethylaminophenyl)thiocarbamidopiperazin-1-yl)phenyl]-2-oxooxazolidin-5-methyl]acetamide;
(S)-N-[3-[3-Fluoro-4-(4-(3-chloro-4-methylphenyl)thiocarbamidopiperazin-1-yl)phenyl]-2-oxooxazolidin-5-methyl]acetamide;
(S)-N-[3-[3-Fluoro-4-(4-(3,4-dichlorophenyl)thiocarbamidopiperazin-1-yl)phenyl]-2-oxooxazolidin-5-methyl]acetamide;
(S)-N-[3-[3-Fluoro-4-(4-(4-cyanophenyl)thiocarbamidopiperazin-1-yl)phenyl]-2-oxooxazolidin-5-methyl]acetamide;
(S)-N-[3-[3-Fluoro-4-(4-(cyclopropyl)thiocarbamidopiperazin-1-yl)phenyl]-2-oxooxazolidin-5-methyl]acetamide ;
(S)-N-[3-[3-Fluoro-4-(4-(cyclooctyl)thiocarbamidopiperazin-1-yl)phenyl]-2-oxooxazolidin-5-methyl]acetamide;
(S)-N-[3-[3-Fluoro-4-(4-(pyridin-3-yl)thiocarbamidopiperazin-1-yl)phenyl]-2-oxooxazolidin-5-methyl]acetamide ;
(S)-N-[3-[3-Fluoro-4-(4-(cyclopentyl)thiocarbamidopiperazin-1-yl)phenyl]-2-oxooxazolidin-5-methyl]acetamide;
(S)-N-[3-[3-Fluoro-4-(4-(cyclohexyl)thiocarbamidopiperazin-1-yl)phenyl]2-oxooxazolidin-5-methyl]acetamide;
(S)-N-[3-[3-Fluoro-4-(4-(4-nitrophenyl)thiocarbamidopiperazin-1-yl)phenyl]-2-oxooxazolidin-5-methyl]acetamide;
(S)-N-[3-[3-Fluoro-4-(4-(4-nitrophenyl)carbamidopiperazin-1-yl)phenyl]-2-oxooxazolidin-5-methyl]acetamide ;
(S)-N-[3-[3-Fluoro-4-(4-(4-benzoyl)thiocarbamidopiperazin-1-yl)phenyl]-2-oxooxazolidin-5-methyl]acetamide;
(S)-N-[3-[3-Fluoro-4-(4-(1,3-benzodioxol-5-ylmethyl)thiocarbamidopiperazin-1-yl)phenyl]-2-oxooxazolidin-5-methyl]acetamide;
(S)-N-[3-[3-Fluoro-4-(4-(propenyl)carbamidopiperazin-1-yl)phenyl]-2-oxooxazolidin-5-methyl]acetamide;
(S)-N-[3-[3-Fluoro-4-(4-(phenyl)thiocarbamidopiperazin-1yl)phenyl]-2-oxooxazolidin-5-methyl]acetamide ;
(S)-N-[3-[3-Fluoro-4-(4-methylthiocarbamidopiperazin-1-yl)phenyl]-2-oxooxazolidin-5methyl]acetamide;
(S)-N-[3-[3-Fluoro-4-(4-(4-nitrophenyl)thiocarbamidopiperazin-1-yl)phenyl]-2-oxooxazolidin-5-methylthioacetamide;
(S)-N-[3-[3-Fluoro-4-(4-(4-nitrophenyl)carbamidopiperazin-1-ylphenyl]-2-oxooxazolidin-5-methyl]thioacetamide;
(S)-N-[3-[3-Fluoro-4-(4-(4-benzoyl)carbamidopiperazin-1-yl)phenyl]-2-oxooxazolidin-5-methyl]thioacetamide;
(S)-N-[3-[3-Fluoro-4-(4-(1,3-benzodioxol-5-ylmethyl)thiocarbamidopiperazin-1-yl)phenyl]-2-oxooxazolidin-5-methyl]thioacetamide;
(S)-N-[3-[3-Fluoro-4-(4-(propenyl)carbamidopiperazin-1-yl)phenyl]-2-oxooxazolidin-5-methyl]thioacetamide;
(S)-N-[3-[3-Fluoro-4-[4-(imidazol-2-ylthiocarbonyl)piperazin-1-yl]phenyl]-2-oxooxazolidin-5-ylmethyl]acetamide;
(S)-N-[3-[3-Fluoro-4-[4-(5-methyl-1,2,4-triazoly-3-ylthiocarbonyl)piperazin-1-yl]phenyl]-2-oxooxazolidin-5-ylmethyl]thioacetamide;
(S)-N-[3-[3-Fluoro-4-[4-(5-methyl-1,2,4-triazoly-3-ylthiocarbonyl)piperazin-1-yl]phenyl]-2-oxooxazolidin-5-ylmethyl]acetamide;
(S)-N-[3-[3-Fluoro-4-[4-(5-ethyl-1,2,4-triazoly-3-ylthiocarbonyl)piperazin-1-yl]phenyl]-2-oxooxazolidin-5-ylmethyl]thioacetamide;
(S)-N-[3-[3-Fluoro-4-[4-(5-ethyl-1,2,4-triazoly-3-ylthiocarbonyl)piperazin-1-yl]phenyl]-2-oxooxazolidin-5-ylmethyl]ethyl]acetamide;
(S)-N-[3-[3-Fluoro-4-[4-(piperazin-2-ylthiocarbonyl)piperazin-1-yl]phenyl]-2-oxooxazolidin-5-ylmethyl]thioacetamide;
(S)-N-[3-[3-Fluoro-4-[4-(piperazin-2-ylthiocarbonyl)piperazin-1-yl]phenyl]-2-oxooxazolidin-5-ylmethyl]acetamide;
(S)-N-[3-[3-Fluoro-4-[4-(1,3,4-oxadiazol-2-ylthiocarbonyl)piperazin-1-yl]phenyl]-2-oxooxazolidin-5-ylmethyl]thioacetamide;
(S)-N-[3-[3-Fluoro-4-[4-(1,3,4-oxadiazol-2-ylthiocarbonyl)piperazin-1-yl]phenyl]-2-oxooxazolidin-5-ylmethyl]acetamide;
(S)-N-[3-[3-Fluoro-4-[4-(5-methyl-1,3,4-oxadiazol-2-ylthiocarbonyl)piperazin-1-yl]phenyl]-2-oxooxazolidin-5-ylmethyl]thioacetamide;
(S)-N-[3-[3-Fluoro-4-[4-(5-methyl-1,3,4-oxadiazol-2-ylthiocarbonyl)piperazin-1-yl]phenyl]-2-oxooxazolidin-5-ylmethyl]acetamide;
(S)-N-[3-[3-Fluoro-4-[4-(1,3,4-thiadiazol-2-ylthiocarbonyl)piperazin-1-yl]phenyl]-2-oxooxazolidin-5-ylmethyl]thioacetamide;
(S)-N-[3-[3-Fluoro-4-[4-(1,3,4-thiadiazol-2-ylthiocarbonyl)piperazin-1-yl]phenyl]-2-oxooxazolidin-5-ylmethyl]acetamide;
(S)-N-[3-[3-Fluoro-4-[4-(1,3,4-oxadiazol-2-ylthioacetyl)piperazin-1-yl]phenyl]-2-oxooxazolidin-5-ylmethyl]thioacetamide;
(S)-N-[3-[3-Fluoro-4-[4-(1,3,4-oxadiazol-2-ylthioacetyl)piperazin-1-yl]phenyl]-2-oxooxazolidin-5-ylmethyl]acetamide;
(S)-N-[3-[3-Fluoro-4-[4-(5-methylimidazol-2-ylthiocarbonyl)piperazin-1-yl]phenyl]-2-oxooxazolidin-5-ylmethyl]thioacetamide;
(S)-N-[3-[3-Fluoro-4-[4-(5-methylimidazol-2-ylthiocarbonyl)piperazin-1-yl]phenyl]-2-oxooxazolidin-5-ylmethyl]acetamide;
(S)-N-[3-[3-Fluoro-4-[4-(1,2,4-triazol-3-ylthiocarbonyacetyl)piperazin-1-yl]phenyl]-2-oxooxazolidin-5-ylmethyl]thioacetamide;
(S)-N-[3-[3-Fluoro-4-[4-(1,2,4-triazol-3-ylthiocarbonyacetyl)piperazin-1-yl]phenyl]-2-oxooxazolidin-5-ylmethyl]acetamide;
(S)-N-[3-[3-Fluoro-4-[4-(5-methyl-1,3,4-thiadiazol-2-ylthiocarbonyl)piperazin-1-yl]phenyl]-2-oxooxazolidin-5-ylmethyl]acetamide;
(S)-N-[3-[3-Fluoro-4-[4-(5-methyl-1,3,4-thiadiazol-2-ylthiocarbonyl)piperazin-1-yl]phenyl]-2-oxooxazolidin-5-ylmethyl]thioacetamide;
(S)-N-[3-[3-Fluoro-4-[4-(5-methyloxazol-2-ylthiocarbonyl)piperazin-1-yl]phenyl]-2-oxooxazolidin-5-ylmethyl]thioacetamide;
(S)-N-[3-[3-Fluoro-4-[4-(5-methyloxazol-2-ylthiocarbonyl)piperazin-1-yl]phenyl]-2-oxooxazolidin-5-ylmethyl]acetamide;
(S)-N-[3-[3-Fluoro-4-[4-(oxazol-2-ylthiocarbonyl)piperazin-1-yl]phenyl]-2-oxooxazolidin-5-ylmethyl]thioacetamide;
(S)-N-[3-[3-Fluoro-4-[4-(oxazol-2-ylthiocarbonyl)piperazin-1-yl]phenyl]-2-oxooxazolidin-5-ylmethyl]acetamide;
(S)-N-[3-[3-Fluoro-4-[4-(2-methyloxazol-5-ylthiocarbonyl)piperazin-1-yl]phenyl]-2-oxooxazolidin-5-ylmethyl]thioacetamide;

(S)-N-[3-[3-Fluoro-4-[4-(2-methyloxazol-5-ylthiocarbonyl)piperazin-1-yl]phenyl]-2-oxooxazolidin-5-ylmethyl]acetamide;
(S)-N-[3-[3-fluoro-4-[4-(2-aminothiopropionyl)piperazin-1-yl]phenyl]-2-oxooxazolidin-5-ylmethyl]acetamide;
(S)-N-[3-[3-fluoro-4-[4-(2-aminothiopropionyl)piperazin-1-yl]phenyl]-2-oxooxazolidin-5-ylmethyl]thioacetamide;
(S)-N-[3-[3-Fluoro-4-[4-(piperadin-2-ylthiocarbonyl)piperazin-1-yl]phenyl]-2-oxooxazolidin-5-ylmethyl]thioacetamide;
(S)-N-[3-[3-Fluoro-4-[4-(piperadin-2-ylthiocarbonyl)piperazin-1-yl]phenyl]-2-oxooxazolidin-5-ylmethyl]acetamide;
(S)-N-[3-[3-Fluoro-4-[4-(piperadin-3-ylthiocarbonyl)piperazin-1-yl]phenyl]-2-oxooxazolidin-5-ylmethyl]thioacetamide;
(S)-N-[3-[3-Fluoro-4-[4-(piperadin-3-ylthiocarbonyl)piperazin-1-yl]phenyl]-2-oxooxazolidin-5-ylmethyl]acetamide;
(S)-N-[3-[3-Fluoro-4-[4-(piperadin-4-ylthiocarbonyl)piperazin-1-yl]phenyl]-2-oxooxazolidin-5-ylmethyl]thioacetamide;
(S)-N-[3-[3-Fluoro-4-[4-(piperadin-4-ylthiocarbonyl)piperazin-1-yl]phenyl]-2-oxooxazolidin-5-ylmethyl]acetamide;
(S)-N-[3-[3-Fluoro-4-[4-(oxazol-5-ylthiocarbonyl)piperazin-1-yl]phenyl]-2-oxooxazolidin-5-ylmethyl]acetamide;
(S)-N-[3-[3-Fluoro-4-[4-(oxazol-5-ylthiocarbonyl)piperazin-1-yl]phenyl]-2-oxooxazolidin-5-ylmethyl]thioacetamide;
(S)-N-[3-[3-Fluoro-4-[4-(morpholin-4-ylcarbonyl)piperazin-1-yl]phenyl]-2-oxooxazolidin-5-ylmethyl]acetamide and
(S)-N-[3-[3-Fluoro-4-[4-(morpholin-4-ylcarbonyl)piperazin-1-yl]phenyl]-2-oxooxazolidin-5-ylmethyl]acetamide.

According to another embodiment of the present invention, there is provided a process for the preparation of novel oxazolidinone derivatives of the formula (I) wherein all symbols are as defined earlier, which comprises:

i) deprotecting the compound of the formula (IIIa)

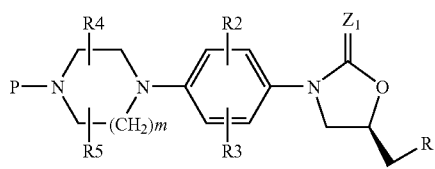

(IIIa)

where P represents protecting group and all other symbols are as defined earlier to produce compound of formula (IIIb)

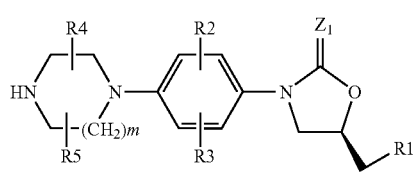

(IIIb)

wherein all symbols are as defined earlier and ii) reacting the compound of formula (IIIb) with a compound of formula (IIIc)

(IIIc)

where $L_1$ is as leaving group and all other symbols are as defined earlier.

The deprotection of compound of formula (IIIa) may be carried out by passing in the presence of solvent selected from acetonitrile, dichloromethane, methanol, dimethylsulfoxide, dimethylformamide, tetrahydrofuran, trifluoro acetic acid, 1-methyl-2-pyrrolidinone, N,N-dimethylacetamide and the like or mixtures thereof. The deprotection may also be carried out using Pd/C in the presence of solvents.

The reaction of compound of formula (IIIb) with compound of formula (IIIc) may be carried out in the presence of base such as triethyl amine, pyridine, DMAP, sodium hydroxide, potassium hydroxide and the like or mixture thereof and solvents such as toluene, DMF, tetrahydrofuran, chloroform, dichloromethane, dichloroethane, dioxane, ethylacetate, o-dichlorobenzene or a mixture thereof. The reaction may be carried out at a temperature in the range of 0° C. to room temperature. The duration of the reaction may range from 1 to 2 hrs.

Alternatively, the reaction of compound of formula (IIIb) with compound of formula (IIIc) may also be carried out using reagent such as dicyclohexylcarbodiimide (DCC), N-hydroxysuccinimide (NHS) and the like in the presence of solvents selected from toluene, DMF, tetrahydrofuran, chloroform, dichloromethane, dichloroethane, dioxane, ethylacetate, o-dichlorobenzene or a mixture thereof.

Alternatively, the reaction of compound of formula (IIIb) with compound of formula (IIIc) may also be carried out using reagent such as 1-ethyl-3-(3-dimethylaminopropyl)carbodiimide (EDAC), 1-hydroxybenztriazole hydrate (HOBt) and the like in the presence of base such as triethyl amine, pyridine, DMAP, and the like and solvents such as toluene, DMF, tetrahydrofuran, chloroform, dichloromethane, dichloroethane, ethylacetate, o-dichlorobenzene or a mixture thereof.

In yet another embodiment of the present invention, there is provided a process for the preparation of novel oxazolidinone derivatives of the formula (I) where $R^1$ represents —NHC(=Y)$R^8$, where Y represents S or O and all other symbols are as defined earlier, which comprises:

a) reacting a compound of the formula (IIId)

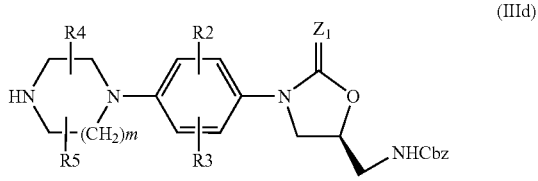

(IIId)

where $L_1$ is as leaving group and A is as defined earlier with a compound of formula (IIIe)

(IIIe)

wherein all symbols are as defined earlier to produce compound of formula (IIIf),

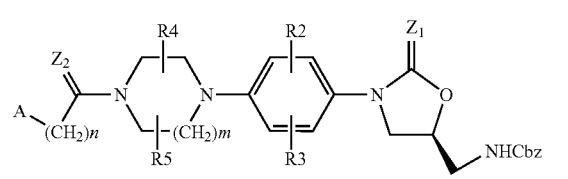

(IIIf)

wherein all symbols are as defined earlier, b) reducing the compound of formula (IIIf) to produce a compound of formula (IIIg)

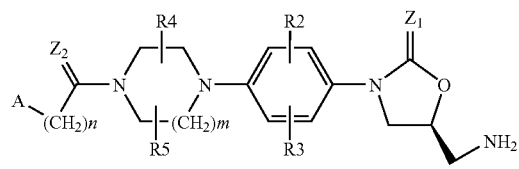

(IIIg)

wherein all symbols are as defined earlier, c) acylating the compound of formula (IIIg) to produce a compound of formula (1) where all symbols are as defined earlier.

The reaction of compound of formula (IIId) with compound of formula (IIIe) may be carried out in the presence of base such as triethyl amine, pyridine and the like and solvents such as toluene, DCC, tetrahydrofuran, chloroform, dichloromethane, dichloroethane, ethylacetate, o-dichlorobenzene or a mixture thereof. The reaction may be carried out at a temperature in the range of 0° C. to room temperature. The duration of the reaction may range from 1 to 2 hrs.

The reduction of compound of formula (IIIf) may be carried out using catalyst such as Pd/C. The reaction may be carried out in the presence of solvents such as toluene, DCC, tetrahydrofuran, chloroform, dichloromethane, dichloroethane, ethylacetate, o-dichlorobenzene or a mixture thereof. The reaction may be carried out at a temperature in the range of 0° C. to room temperature. The duration of the reaction may range from 1 to 2 hrs.

Acylation of compound of formula (IIIg) may be carried out using acylating agents such as anhydrides like acetic anhydride, propionic anhydride, acid chlorides like acetyl chloride, propionyl chloride, thioacids such as thioacetic acid. The reaction may be carried out in the presence of appropriate solvents like tetrahydrofuran, chloroform, dichloromethane, dichloroethane, ethylacetate, o-dichlorobenzene or a mixture thereof. The reaction may be carried out at a temperature in the range of 0° C. to room temperature. The duration of the reaction may range from 6 to 12 hrs.

In yet another embodiment of the present invention, there is provided a process for the preparation of compounds of formula (I) where $R^1$ represents $XR^6$, $N(R^{7a}R^{7b})$, wherein $R^6$, $R^{7a}$ and $R^{7b}$ are as defined earlier which comprises reacting the compound of formula (IIIh)

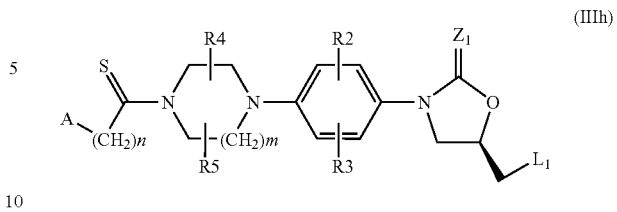

(IIIh)

where $L^1$ represents a leaving group such as mesylate, tosylate or triflate with $R^6XH$ or $NH(R^{7a}R^{7b})$ where all symbols are as defined earlier.

The conversion of compounds of formula (IIIh) to a compound of formula (1) may be carried out by heating in the presence of base selected from NaH, KH, t-BuOK and the like and solvents such as DMF, THF, DCM, DMA and the like. The reaction temperature may range from 0° C. to room temperature. The duration of the reaction may range from 2 to 6 hrs.

In yet another embodiment of the present invention, there is provided a process for the preparation of compounds of formula (I) wherein $R^1$ represents $—NHS(O)_r(C_1–C_4)alkyl$, $—NHS(O)_r aralkyl$ or $—NHS(O)_r heteroaralkyl$ group, which comprises reacting the compound of formula (IIIg)

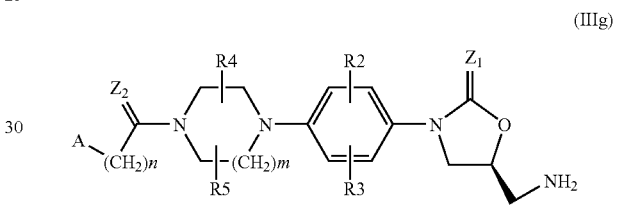

(IIIg)

where all symbols are as defined earlier which represents compounds of formula (I), $R^1$ represents $N(R^{7a}R^{7b})$ where $R^{7a}$ and $R^{7b}$ represent hydrogen, with $R'SO_2Cl$ where $R'$ represents $(C_1–C_4)alkyl$, aralkyl or heteroaralkyl group.

The reaction of compounds of formula (IIIg) may be carried out by heating in the presence of base selected from pyridine, triethylamine and the like and solvents such as DMF, DCM, ethyl acetate and the like. The reaction temperature may range from 0° C. to room temperature. The duration of the reaction may range from 4 to 12 hrs.

According to another embodiment of the present invention, there is provided a process for the preparation of novel oxazolidinone derivatives of the formula (I) where $R^1$ represents the formula $—NHC(=Y)R^8$ where Y is O or S, $R^8$ and all other symbols are as defied above, which comprises:

i) reacting a compound of the formula (IIIi)

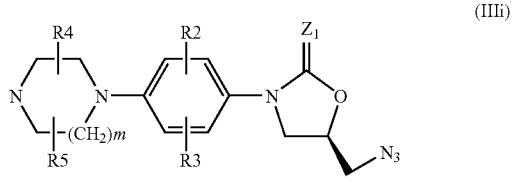

(IIIi)

where all symbols are as defined earlier with a compound of formula (IIIb)

(IIIb)

where $L_1$ is as leaving group and all other symbols are as defined earlier to produce compound of formula (IIIj)

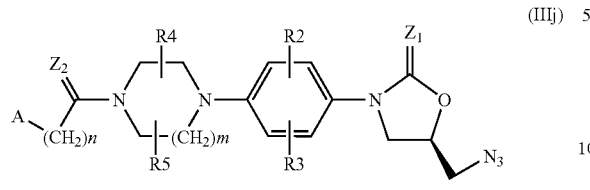

wherein all symbols are as defined earlier and b) acylating the compound of formula (IIIj) to produce compound of formula (I), where all symbols are as defined earlier.

The reaction of compound of formula (IIIi) with compound of formula (IIIb) may be carried out in the presence of base such as triethyl amine, pyridine, DMAP, and the like and solvents such as toluene, DMF, tetrahydrofuran, chloroform, dichloromethane, dichloroethane, ethylacetate, o-dichlorobenzene or a mixture thereof. The reaction may be carried out using reagent such as 1-ethyl-3-(3-dimethylaminopropyl)carbodiimide (EDAC), 1-hydroxybenztriazole hydrate (HOBt) and the like. The reaction may be carried out at a temperature in the range of 0° C. to room temperature. The duration of the reaction may range from 1 to 2 hrs.

The acylation of compound of formula (IIIj) may be carried out using acylating agents such as thioacetic acid. The reaction may be carried out in the presence of appropriate solvents like tetrahydrofuran, chloroform, dichloromethane, dichloroethane, ethylacetate, o-dichlorobenzene or a mixture thereof. The reaction may be carried out at a temperature in the range of 0° C. to room temperature. The duration of the reaction may range from 6 to 12 hrs.

In yet another embodiment of the present invention, there is provided a process for the preparation of novel oxazolidinone derivatives of the formula (I) wherein $R^1$ represents —NHC(=Y)$R^8$, where Y represents S and all other symbols are as defined earlier, which comprises:

i) reacting the compound of the formula (IIIa)

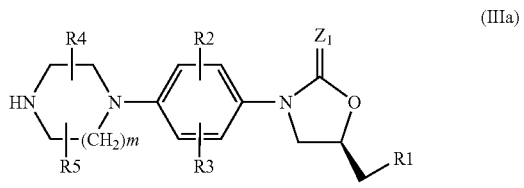

wherein $R^1$ represents —NHC(=Y)$R^8$ where Y is O or S, $R^8$ is as defined earlier with compound of formula (IIIl)

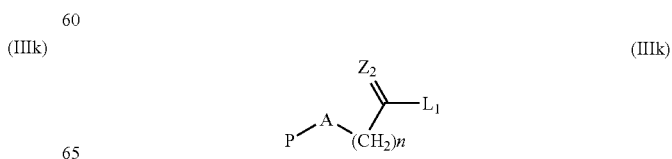

wherein P represents a protecting group all symbols are as defined earlier to yield compound of formula (IIIl)

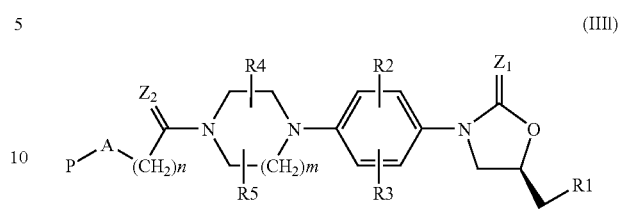

wherein $R^1$ represents —NHC(=Y)$R^8$ where Y is O or S, $R^8$ is as defined earlier and all other symbols are as defined above, ii) deprotecting the compound of formula (IIIl) to produce compound of formula (I) where all symbols are as defined above.

The reaction of compound of formula (IIIa) with compound of formula (IIIk) may be carried out in the presence of base such as triethyl amine, pyridine, DMAP, and the like and solvents such as toluene, DMF, tetrahydrofuran, chloroform, dichloromethane, dichloroethane, ethylacetate, o-dichlorobenzene or a mixture thereof. The reaction may be carried out using reagent such as 1-ethyl-3-(3-dimethylaminopropyl)carbodiimide (EDAC), 1-hydroxybenztriazole hydrate (HOBt) and the like. The reaction may be carried out at a temperature in the range of 0° C. to room temperature. The duration of the reaction may range from 1 to 2 hrs.

The deprotection of compound of formula (IIIl) is carried out by passing HCl gas in the presence of solvent selected from acetonitrile, dichloromethane, methanol, dimethylsulfoxide, dimethylformamide, tetrahydrofuran, 1-methyl-2-pyrrolidinone, N,N-dimethylacetamide and the like or mixtures thereof. The reaction may be carried out at a temperature in the range of −10 to 30° C.

In yet another embodiment of the present invention, there is provided a process for the preparation of novel oxazolidinone derivatives of the formula (I) wherein $R^1$ represents —NHC(=Y)$R^8$, where Y represents O or S and all other symbols are as defined earlier, which comprises:

i) reacting the compound of the formula (IIIi)

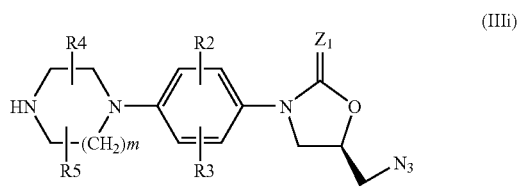

wherein $R^1$ represents —NHC(=Y)$R^5$ where Y is O or S, $R^8$ is as defined earlier with compound of formula (IIIk)

wherein P represents a protecting group all symbols are as defined earlier to yield compound of formula (IIIm)

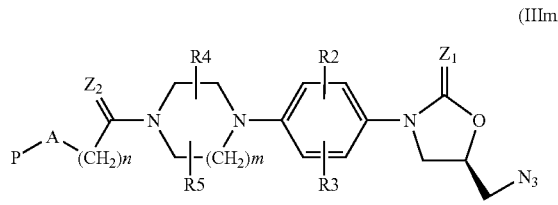
(IIIm)

wherein all symbols are as defined above, ii) acylating the compound of formula (IIIm) to produce a compound of formula (IIII)

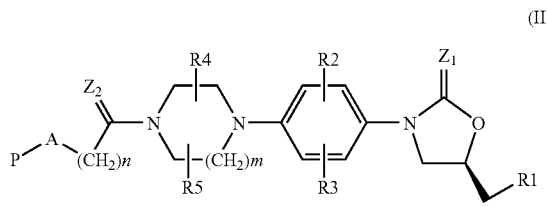
(IIII)

wherein $R^1$ represents —NHC(=Y)$R^8$ where Y is O or S, $R^8$ is as defined earlier and all other symbols are as defined above, iii) deprotecting the compound of formula (IIII) to produce compound of formula (I) where all symbols are as defined above.

The reaction of compound of formula (IIIi) with compound of formula (IIIk) may be carried out in the presence of base such as triethyl amine, pyridine, DMAP, and the like and solvents such as toluene, DMF, tetrahydrofuran, chloroform, dichloromethane, dichloroethane, ethylacetate, o-dichlorobenzene or a mixture thereof. The reaction may be carried out using reagent such as 1-ethyl-3-(3-dimethylaminopropyl)carbodiimide (EDAC), 1-hydroxybenztriazole hydrate (HOBt) and the like. The reaction may be carried out at a temperature in the range of 0° C. to room temperature. The duration of the reaction may range from 1 to 2 hrs.

Acylation of compound of formula (IIIm) may be carried out using acylating agents such as anhydrides like acetic anhydride, propionic anhydride, acid chlorides like acetyl chloride, propionyl chloride, thioacids such as thioacetic acid. The reaction may be carried out in the presence of appropriate solvents like tetrahydrofuran, chloroform, dichloromethane, dichloroethane, ethylacetate, o-dichlorobenzene or a mixture thereof. The reaction may be carried out at a temperature in the range of 0° C. to room temperature. The duration of the reaction may range from 6 to 12 hrs.

The deprotection of compound of formula (IIII) is carried out by passing HCl gas in the presence of solvent selected from acetonitrile, dichloromethane, methanol, dimethylsulfoxide, dimethylformamide, tetrahydrofuran, 1-methyl-2-pyrrolidinone, N,N-dimethylacetamide and the like or mixtures thereof. The reaction may be carried out at a temperature in the range of −10 to 30 ° C.

In another embodiment of the present invention, there is provided a process for the preparation of compounds where any of the groups Y and $Z^2$ represent O to compounds where Y and $Z^2$ represent S using Lawesson's reagent. The reaction may be may be carried out in the presence of base such as triethyl amine, pyridine and the like and solvents such as toluene, DCC, tetrahydrofuran, chloroform, dichloromethane, dichloroethane, ethylacetate, o-dichlorobenzene or a mixture thereof. The reaction may be carried out at a temperature in the range of 0° C. to room temperature. The duration of the reaction may range from 1 to 2 hrs.

The protecting groups used in the invention are conventional protecting groups such as t-butoxy carbonyl (t-Boc), acetyl, trityl, trifluoroacetyl, benzyloxy, 9-fluorenyl methylcarbonate (Fmoc), vinyl carbamate, benzyloxy carbonyl (Cbz), 2,2,2-trichloroethyl carbamate (Troc), allyl carbamate.

It is appreciated that in any of the above-mentioned reactions, any reactive group in the substrate molecule may be protected according to conventional chemical practice. Suitable protecting groups in any of the above-mentioned reactions are those used conventionally in the art. The methods of formation and removal of such protecting groups are those conventional methods appropriate to the molecule being protected.

The pharmaceutically acceptable salts are prepared by reacting the compound of formula (I) with 1 to 4 equivalents of a base such as sodium hydroxide, sodium methoxide, sodium hydride, potassium t-butoxide, calcium hydroxide, magnesium hydroxide and the like, in solvents like ether, tetrahydrofuran, methanol, t-butanol, dioxane, isopropanol, ethanol etc. Mixture of solvents may be used. Organic bases such as diethanolamine, α-phenylethylamine, benzylamine, piperidine, morpholine, pyridine, hydroxyethylpyrrolidine, hydroxyethylpiperidine, choline and the like, ammonium or substituted ammonium salts, aluminum salts. Amino acid such as glycine, alanine, cystine, cysteine, lysine, arginine, phenylalanine, guanidine etc may be used for the preparation of amino acid salts. Alternatively, acid addition salts wherever applicable are prepared by the treatment with acids such as hydrochloric acid, hydrobromic acid, nitric acid, sulfuric acid, phosphoric acid, p-toluenesulphonic acid, methanesulfonic acid, acetic acid, citric acid, maleic acid, salicylic acid, hydroxynaphthoic acid, ascorbic acid, palmitic acid, succinic acid, benzoic acid, benzenesulfonic acid, tartaric acid and the like in solvents like ethyl acetate, ether, alcohols, acetone, tetrahydrofuran, dioxane etc. Mixture of solvents may also be used.

The stereoisomers of the compounds forming part of this invention may be prepared by using reactants in their single enantiomeric form in the process wherever possible or by conducting the reaction in the presence of reagents or catalysts in their single enantiomer form or by resolving the mixture of stereoisomers by conventional methods. Some of the preferred methods include use of microbial resolution, resolving the diastereomeric salts formed with chiral acids such as mandelic acid, camphorsulfonic acid, tartaric acid, lactic acid, and the like wherever applicable or chiral bases such as brucine, cinchona alkaloids and their derivatives and the like. Commonly used methods are compiled by Jaques et al in "Enantiomers, Racemates and Resolution" (Wiley Interscience, 1981). More specifically the compound of formula (I) may be converted to a 1:1 mixture of diastereomeric amides by treating with chiral amines, aminoacids, aminoalcohols derived from aminoacids; conventional reaction conditions may be employed to convert acid into an amide; the diastereomers may be separated either by fractional crystallization or chromatography and the stereoisomers of compound of formula (I) may be prepared by hydrolysing the pure diastereomeric amide.

Various polymorphs of compound of general formula (I) forming part of this invention may be prepared by crystallization of compound of formula (1) under different conditions. For example, using different solvents commonly used or their mixtures for recrystallization; crystallizations at different temperatures; various modes of cooling, ranging from very fast to very slow cooling during crystallizations. Polymorphs may also be obtained by heating or melting the compound followed by gradual or fast cooling. The presence of polymorphs may be determined by solid probe nmr spectroscopy, ir spectroscopy, differential scanning calorimetry, powder X-ray diffraction or such other techniques.

Pharmaceutically acceptable solvates of the compounds of formula (I) forming part of this invention may be prepared by conventional methods such as dissolving the compounds of formula (I) in solvents such as water, methanol, ethanol, mixture of solvents such as acetone:water, dioxane:water, N,N-dimethylformamide:water and the like, preferably water and recrystallizing by using different crystallization techniques.

The present invention provides a pharmaceutical composition, containing the compounds of the general formula (I) as defined above, their derivatives, their analogs, their tautomeric forms, their stereoisomers, their polymorphs, their pharmaceutically acceptable hydrates and solvates in combination with the usual pharmaceutically employed carriers, diluents and the like, useful for the treatment of inflammation, arthritis, pain, fever, psoriasis, allergic diseases, asthma, inflammatory bowel syndrome, gastro-intestinal ulcers, cardiovascular disorders including ischemic heart disease, atherosclerosis, cancer, ischemic-induced cell damage, particularly brain damage caused by stroke, other pathological disorders associated with free radicals.

The pharmaceutical composition may be in the forms normally employed, such as tablets, capsules, powders, syrups, solutions, suspensions and the like, may contain flavoring agents, sweeteners etc. in suitable solid or liquid carriers or diluents, or in suitable sterile media to form injectable solutions or suspensions. Such compositions typically contain from 1 to 20%, preferably 1 to 10% by weight of active compound, the remainder of the composition being pharmaceutically acceptable carriers, diluents or solvents.

The present invention is provided by the examples below, which are provided by way of illustration only and should not be considered to limit the scope of the invention.

Preparation 1

Preparation of 3-fluoro-4-piperazine nitrobenzene

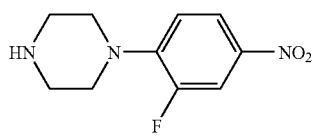

To a solution of 3,4-difluoronitrobenzene (11.07 ml, 100 mmole) in acetonitrile (200 ml) piperazine (21.53 g, 250 mmoles) was added portion wise and the resulting mixture was stirred at room temperature until solution became homogeneous. The reaction mixture was then heated to 80° C. for 6 hrs. Excess acetonitrile was evaporated under reduced pressure and the reaction mixture was taken with water (150 ml) and ethyl acetate (2×250 ml), organic layers were pooled, dried over $Na_2SO_4$, solvent removed and purified using silica gel column using 30% MeOH in EtOAc to afford the title compound (23 g, yield 98%).

Preparation 2

Preparation of 3-fluoro-4(N-t-butoxycarbonylpiperazin-1-yl)nitrobenzene

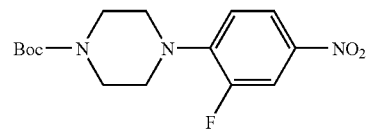

3-Fluoro-4-piperazine nitrobenzene (18.3 g, 81 mmole) (obtained according to the procedure described in preparation 1) was dissolved in TBF (80 ml) and added di-tert. butyl dicarbonate (24.1 ml, 105.3 mmol) in THF (50 ml) at 0° C. The resulting mixture was brought to ambient temperature and stirred until reaction was complete. The product was extracted with ethyl acetate and purified to afford the title compound (23 g).

Preparation 3

Preparation of 3-fluoro(N-t-butoxycarbonylpiperazin-1-yl)aniline

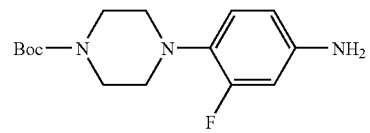

To a solution of 3-fluoro-4-(N-t-butoxycarbonylpiperazin-1-yl)nitrobenzene (23 g, 72 mmol) (obtained according to the procedure described in preparation 2) in EtOAc (450 ml) 10% Pd/C(1.79 g) was added in portions while stirring. The reduction was carried out in the presence of $H_2$ atmosphere maintained by inserting hydrogen balloon. After the reaction was over (12–14 hrs.), the contents were filtered through a celite bed. The solvent was removed from the filtrate under vacuum to provide the title compound (19.7 g, yield 93%), which was used for the next step without further purification.

Preparation 4

Preparation of 3-fluoro-4—N-t-butoxycarbonylpiperazin-1-yl)phenylcarbamate

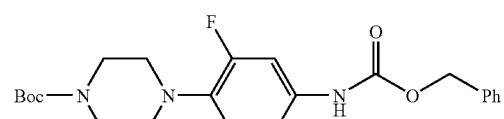

To a solution of 3-fluoro-4-(N-t-butoxycarbonylpiperazin-1-yl)aniline (16.8 g, 57 mmol) (obtained according to the procedure described in preparation 3) in TBF (30 ml), dimethyl aniline (7.92 ml, 62.7 mmol) was added. To this benzyl chloroformate (8.27 ml, 58.14 mmol) dissolved in THF (20 ml) was added over a period of 20 min upon stirring at 0° C. After completion of the reaction, the resulting mixture was quenched with saturated NaCl solution (50 ml) and extracted with EtOAc (3×200 ml). The organic layer was evaporated, dried over $Na_2SO_4$ and purified using silica gel column using 50% EtOAc in hexane to afford the title compound (24 g).

Preparation 5

Preparation of (S)-[3-[3-fluoro-4-[N-t-butoxycarbonylpiperazin-1-yl]phenyl]-2-oxooxazolidin-5-yl]methanol

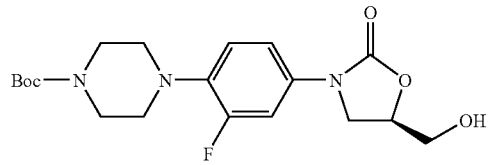

To a solution of 3-fluoro-4-(N-t-butoxycarbonylpiperazin-1-yl)phenylcarbamate (2.14 g, 5 mmol) (obtained according to the procedure described in preparation 4) in dry TFW (40 ml), 15% n-BuLi (8.53 ml) in hexane was added at −78° C. The temperature was maintained at −78° C. while addition and the resulting mixture was allowed to stir for 30 min under $N_2$ atmosphere. Then (R)-glycidylbutyrate (0.85 ml) was added at −78° C. and the temperature bath was removed after 30 min allowing the reaction mixture to stir overnight. Saturated $NH_4Cl$ (50 ml) was added and the product was extracted with EtOAc (3×300 ml), dried over $Na_2SO_4$ and evaporated to dryness and purified using silica gel column using EtOAc as the eluent to obtain the title compound (1.45 g).

Preparation 6

Preparation of (S)-[3-[3-fluoro-4-[N-t-butoxycarbonylpiperazin-1-yl]phenyl]-2-oxooxazolidin-5-yl]mesylate

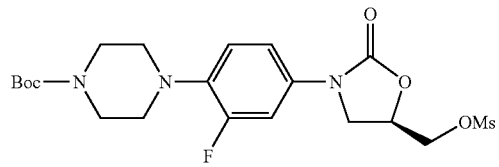

To a solution of (S)-[3-[3-fluoro-4-[N-t-butoxycarbonylpiperazin-1-yl]phenyl]-2-oxooxazolidin-5-yl]methanol (1.45 g, 3.6 mmol) (obtained according to the procedure described in preparation 5) in dry DCM (15 ml) $Et_3N$ (0.77 ml) and methane sulphonyl chloride (0.343 ml) was added and the resulting mixture was allowed to stir at 0° C. until the reaction is completed. The product was extracted with EtOAc and the organic layer washed several times with water, dried over $Na_2SO_4$, evaporated the solvent to afford the title compound (1.45 g) which was used further without purification.

Preparation 7

Preparation of (S)-N-[3-[3-fluoro-4-[N-t-butoxycarbonylpiperazin-1-yl]phenyl]-2-oxooxazolidin-5-ylmethyl]azide

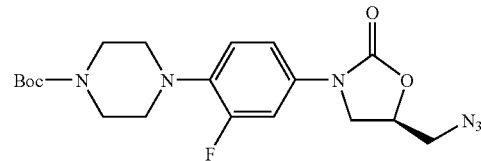

To a solution of (S)-[3-[3-fluoro-4-[N-t-butoxycarbonylpiperazin-1-yl]phenyl]-2-oxooxazolidin-5-yl]mesylate (1.2 g, 2.69 mmol) (obtained according to the procedure described in preparation 6) in DMF (10 ml) sodium azide (613 mg) was added and heated to 80° C. for 4 hr. After completion of the reaction, the product was extracted with EtOAc and water. The organic layer was separated, dried and purified onto a silica gel column using 50% EtOAc in hexane to afford the title compound (1 g).

Preparation 8

Preparation of (S)-N-[3-[3-fluoro-4-[N-t-butoxycarbonylpiperazin-1-yl]phenyl]-2-oxooxazolidin-5-ylmethyl]acetamide

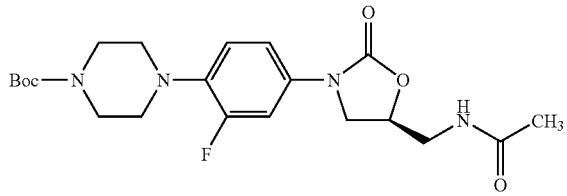

To a solution of (S)-N-[3-[3-fluoro-4-[N-t-butoxycarbonylpiperazin-1-yl]phenyl]-2-oxooxazolidin-5-ylmethyl]azide (0.86 g, 2.06 mmol) (obtained according to the procedure described in preparation 7) in EtOAc (50 ml), 5% Pd/C (72 mg) was added and the reaction mixture was allowed to stir at ambient temperature under $H_2$ balloon condition. After completion of the reduction, pyridine (0.42 ml) and acetic anhydride (1 ml) were added upon stirring. The acetylated product was extracted with EtOAc, washed several times with water and dried over $Na_2SO_4$, evaporated the solvent and purified to afford the title compound (0.79 gm).

Preparation 9

Preparation of (S)-N-[3-[3-fluoro-4-[piperazin-1-yl]phenyl]-2-oxooxazolidin-5-ylmethyl]acetamide

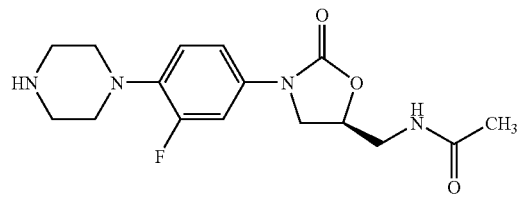

To a solution of (S)-N-[3-[3-fluoro-4-[N-t-butoxycarbonylpiperazin-1-yl]phenyl]-2-oxooxazolidin-5-ylmethyl]acetamide (545 mg, 1.25 mmol) (obtained according to the procedure described in preparation 8) in dry DCM (15 ml) TFA (1.5 ml) in DCM (13.5 ml) was added at 0° C. The mixture was stirred at 0° C. for 2 hrs and then at ambient temperature for additional 3–4 hr. Excess TFA and DCM were evaporated under reduced pressure to obtain a solid mass. The mass was redissolved in DCM (5 ml) and added Et₃N (516 µl) and stirred for 2–3 hrs to afford 3-fluoro-4-[piperazinyl-4-yl]-phenyl]-2-oxazolidin-5-yl]methyl]acetamide.

Preparation 10

Synthesis of (S)N-[3-[3-fluoro-4-[4-(thiophen-3-ylcarbonyl)piperazin-1-yl]phenyl]-2-oxooxazolidin-5-ylmethyl]acetamide

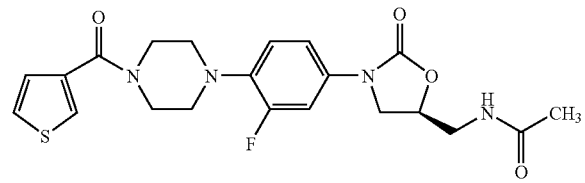

To a solution of 3-fluoro-4-[piperazinyl-4-yl]-phenyl]-2-oxazolidin-5-yl]methyl]acetamide (prepared according to the procedure described in preparation 9) in DMF (5 ml), thiophene 3-carboxylic acid (160 mg, 1.25 mmol), 1-hydroxybenztriazole hydrate (HOBt) (202.7 mg, 1.5 mmol), dichloroethane, (EDC) (597 mg, 3.12 mmol) and DMAP (50 mg) were added and the resulting mixture was stirred for 8 hrs. The product was extracted with EtOAc and water. The organic layer was separated, dried over Na₂SO₄ and solvent was removed under vacuum. The product was purified onto a silica gel column using 20% MeOH in EtOAc to afford the title compound (302 mg, yield 54%).

¹H-NMR (CDCl₃): δ 2.0 (3H, s), 3.0 (4H, m), 3.8 (1H, m), 3.9 (4H, m), 4.3 (3H, m), 5.0 (1H, m), 6.8–7.3 (6H, m, aromatic). Mass: M+1=447

The following compounds were prepared according to the procedure given in preparation 10.

| Preparation No. | Structure | Analytical Data |
| --- | --- | --- |
| 11 | 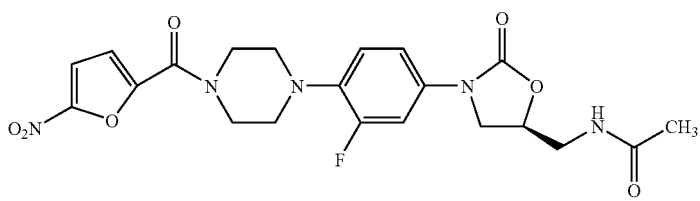 | ¹H-NMR (CDCl₃): δ 2.0(3H, s), 3.2(4H, m), 3.8(2H, m), 4.0(4H, m), 4.3(2H, m), 5.1(1H, m), 6.9–7.5(5H, m, aromatic). Mass: M + 1 = 476. |
| 12 | 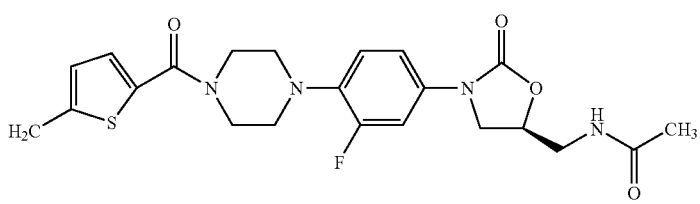 | ¹H-NMR (CDCl₃): δ 2.0(3H, s), 2.1(3H, s), 2.9(4H, m), 3.8(1H, m), 3.9(3H, m), 4.1(4H, m), 5.0(1H, m), 6.6–7.4(5H, m, aromatic). Mass: M + 1: = 461. |
| 13 | 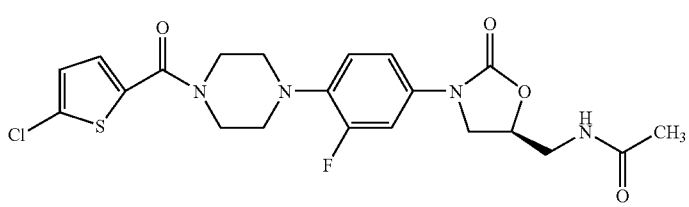 | ¹H-NMR (CDCl₃): δ 2.0(3H, s), 3.0(4H, m), 3.9(1H, m), 4.0(3H, m), 4.3(4H, m), 4.9(1H, m), 6.8–7.4(5H, m, aromatic). Mass: M + 1 = 481. |
| 14 | 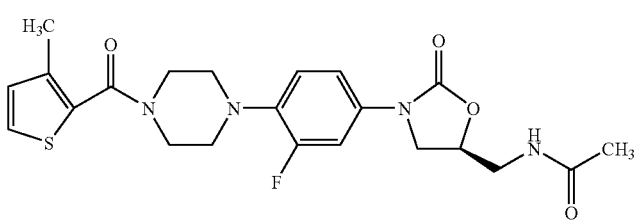 | ¹H-NMR (CDCl₃): δ 2.0(3H, s), 2.1(3H, s), 3.0(4H, m), 3.9(3H, m), 4.0(3H, m), 4.3(1H, m), 4.5(1H, m), 5.0(1H, m), 6.8–7.9(5H, m, aromatic). Mass: M + 1 = 461. |

-continued

| Preparation No. | Structure | Analytical Data |
|---|---|---|
| 15 | 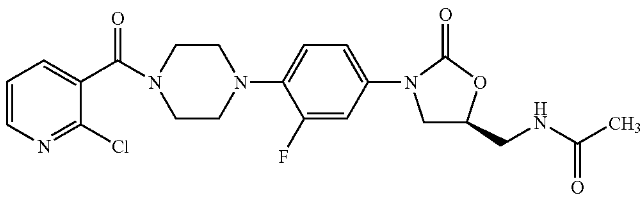 | ¹H-NMR (CDCl₃): δ 2.1(3H, s), 3.2(4H, m), 3.8(2H, m), 3.81(4H, m), 4.1(1H, m), 4.3(1H, m), 5.0(1H, m), 6.7–8.2(6H, m, aromatic). Mass: M + 1 = 476. |
| 16 | 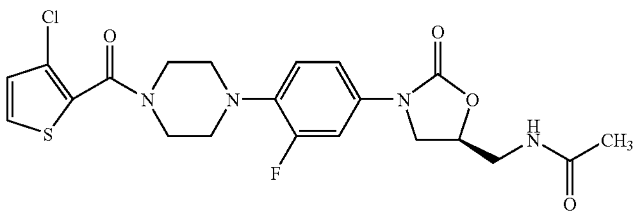 | ¹H-NMR (CDCl₃): δ 2.0(3H, s), 3.0(4H, m), 3.3(1H, m), 3.8(4H, m), 4.0(3H, m), 4.9(1H, m), 6.8–7.5(5H, m, aromatic). Mass: M + 1 = 481. |
| 17 | 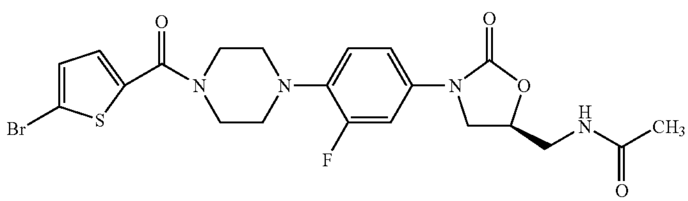 | ¹H-NMR (CDCl₃): δ 2.0(3H, s), 3.0(4H, m), 3.8(2H, m), 3.9(2H, m), 4.0(4H, m), 4.9 3.9(2H, m), 4.0(4H, m), 4.9(1H, m), 6.8–7.5(5H, m, aromatic). Mass: M + 1 = 526. |
| 18 | 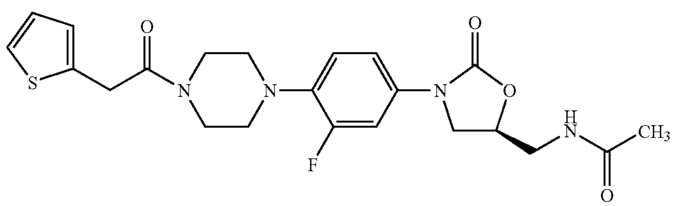 | ¹H-NMR (CDCl₃): δ 2.0(3H, s), 2.8(2H, s), 3.1(2H, m), 3.7(3H, m), 4.0(2H, m), 4.3(1H, m), 4.5(4H, m), 5.0(1H, m), 6.7–7.5(6H, m, aromatic). Mass: M + 1 = 461. |
| 19 | 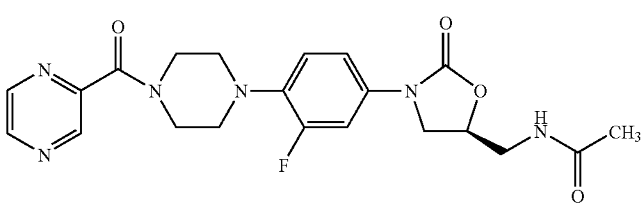 | ¹H-NMR (CDCl₃): δ 2.1(3H, s), 3.0(4H, m), 3.5(4H, m), 4.0(2H, m), 4.5(2H, m), 5.0(1H, m), 6.7–7.2(6H, m, aromatic). Mass: M + 1 = 443. |
| 20 | 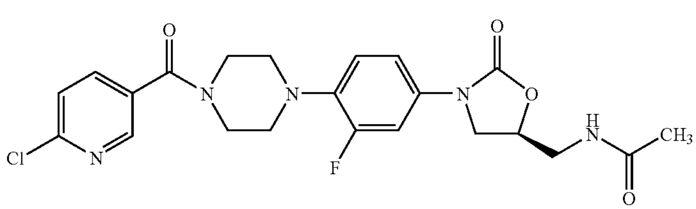 | ¹H-NMR (CDCl₃): δ 2.1(3H, s), 3.2(2H, m), 3.8(6H, m), 3.9(2H, m), 4.5(2H, m), 5.0(1H, m), 6.2–8.3(6H, m, aromatic). Mass: M + 1 = 476. |
| 21 | 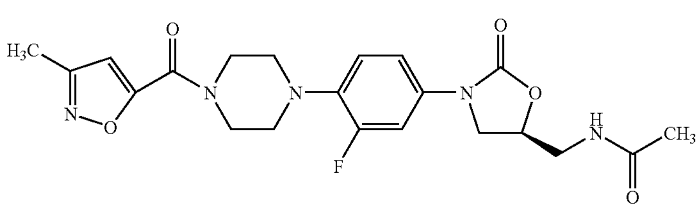 | ¹H-NMR (CDCl₃): δ 1.9(3H, s), 2.0(3H, s), 3.0(4H, m), 3.5(3H, m), 4.0(2H, m), 4.4(1H, m), 4.6(2H, m), 4.9(1H, m), 7.0–7.4(4H, m, aromatic). Mass: M + 1 = 446. |

| Preparation No. | Structure | Analytical Data |
|---|---|---|
| 22 | 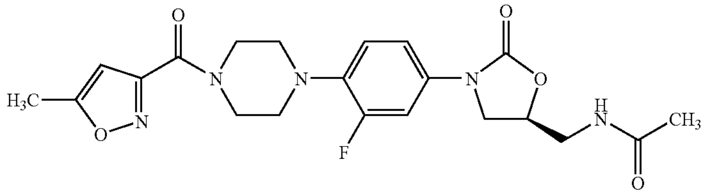 | $^1$H-NMR (CDCl$_3$): δ 2.0(3H, s), 2.1(3H, s), 3.0(4H, m), 3.7(3H, m), 3.9(2H, m), 4.4(1H, m), 4.5(2H, m), 4.9(1H, m), 6.9–7.5(4H, m, aromatic). Mass: M + 1 = 446. |
| 23 | 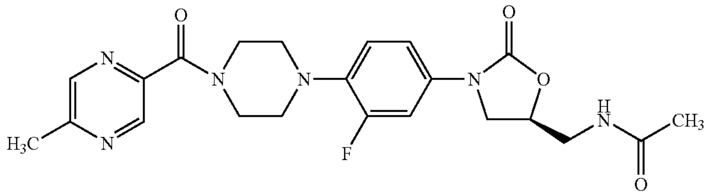 | $^1$H-NMR (CDCl$_3$): δ 2.0(3H, s), 2.1(3H, s), 3.0(4H, m), 3.5(4H, m), 4.0(1H, m), 4.1(1H, m), 4.5(2H, m), 4.9(1H, m), 6.9–7.9(5H, m, aromatic). Mass: M + 1 = 457. |
| 24 | mp : 236° C. | $^1$H-NMR (DMSO D$_6$): δ 1.83(3H, s), 3.04(4H, s), 3.41(2H, t), 3.70(1H, q), 3.80(2H, s), 4.10(1H, t), 4.64(2H, s), 4.70(1H, m), 7.10(2H, t), 7.17(1H, d), 7.26(1H, s), 7.52(1H, dd), 8.24(1H, t), 12.95(1H, s). Mass: M + 1 = 431. |
| 25 | 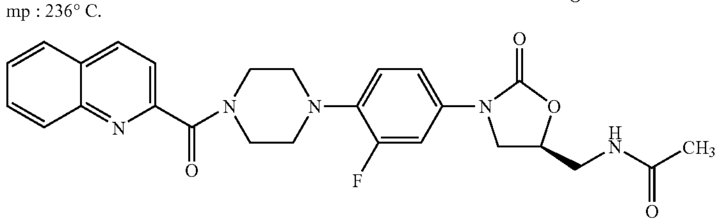 | $^1$H-NMR (CDCl$_3$): δ 2.1(3H, s), 3.3(4H, m), 3.9(3H, m), 4.1(1H, m), 4.4(2H, m), 4.5(2H, m), 4.9(1H, m), 6.9–8.1(9H, m, aromatic). Mass: M + 1 = 492 |

Preparation 26

Synthesis of (S)-N-[3-[3-fluoro-4-[4(thiophen-2-ylcarbonyl)piperazin-1-yl]phenyl]-2-oxooxazolidin-5-ylmethyl]acetamide

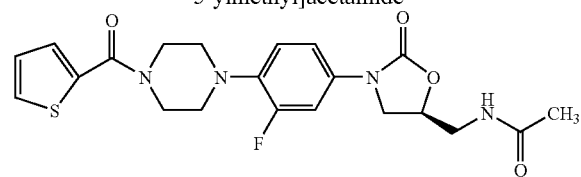

A solution of thiophene-2-carboxylic acid (37 mg, 0.29 mmol) in dioxane (5 ml), NHS (40 mg, 0.36 mmol) and DCC (71 mg, 0.36 mmol) were added allowed to stir at room temperature under N$_2$ atmosphere for 4 hrs. The precipitate of DCC was removed by filtration and the filtrate was added to (S)-N-[3-[3-fluoro-4-[piperazin-1-yl]phenyl]-2-oxooxazolidin-5-ylmethyl]acetamide (prepared according to the procedure described in preparation 9), dissolved in dioxane (10 ml). The reaction was stirred overnight, solvent removed under vacuum, extracted with EtOAc/water and the title compound was purified onto a silica gel column using 10% MeOH in EtOAc to give the title compound (100 mg, yield 90%).

$^1$H-NMR (CDCl$_3$): δ 2.0 (3H, s), 3.1 (4H, m), 3.8 (1H, m), 3.9 (3H, m), 4.3 (2H, m), 4.5 (2H, m), 4.9 (1H, m), 6.9–7.3 (6H, aromatic, m). Mass: M+1=447

The following compounds were prepared according to the procedure given in preparation 26.

| Preparation No. | Structure | Analytical Data |
|---|---|---|
| 27 | 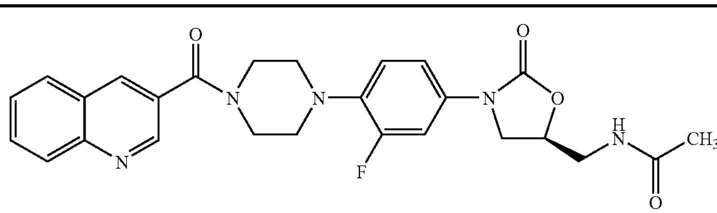 | $^1$H-NMR (CDCl$_3$): δ 2.1(3H, s), 3.1(2H, m), 3.2(2H, m), 3.8(3H, m), 4.1(2H, m), 4.2(1H, m), 4.6(2H, m), 5.0(1H, m), 6.9–8.2 (9H, m, aromatic). Mass: M + 1 = 492. |

Preparation 28

Synthesis of (S)-N-[3-[3-fluoro-4-[4-(cyclopropyl-carbonyl)piperazin-1-yl]phenyl]-2-oxooxazolidin-5-ylmethyl]acetamide

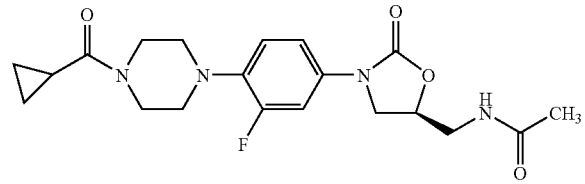

(S)-N-[3-[3-fluoro-4-[N-t-butoxycarbonylpiperazin-1-yl]phenyl]-2-oxooxazolidin-5-ylmethyl]acetamide (200 mg, 0.46 mmol) (preparation according to the procedure described in preparation 8) was treated with TFA/DCM as explained in preparation 9. The TFA salt was dissolved in dry DMF (10 ml) and added K$_2$CO$_3$ (190 mg) and cyclopropane carbonyl chloride (50 μl). The reaction mixture was stirred at room temperature for 10 hrs. The product was extracted with EtOAc/water, dried and purified to provide the title compound (120 mg, yield 65%).

$^1$H-NMR (CDCl$_3$): δ 1.0 (2H, m), 1.3 (2H, m), 2.0 (1H, m), 2.1 (3H, s), 3.2 (4H, m), 3.7 (1H, m), 3.8 (4H, m),4.3 (3H, m), 5.0 (1H, m), 7.0–7.4 (3H, m, aromatic). Mass: M+1=405

Preparation 29

Synthesis of (S)-N-[3-[3-fluoro-4-[4-(benzoyl)piperazin-1-yl]phenyl]-2-oxooxazolidin-5-ylmethyl]acetamide

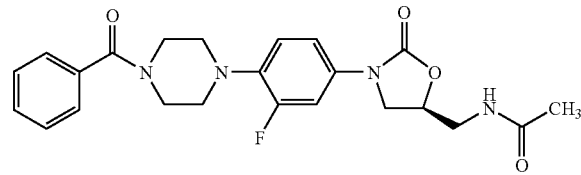

To a solution of 3-fluoro-4-[piperazinyl-4-yl]phenyl]-2-oxazolidin-5-yl]methyl]acetamide (200 mg, 0.47 mmol) (obtained according to the procedure described in preparation 9) in DMF (5 ml) benzoyl chloride (34 μl) was added and the mixture was allowed to stir at the ambient temperature for 15 hrs. The product was extracted with EtOAc and water. The organic layer was separated, dried over Na$_2$SO$_4$ and purified through a silica gel column using 20% MeOH in EtOAc to afford the title compound (110 mg, yield 90%).

$^1$H-NMR (CDCl$_3$): δ 2.1 (3H, s), 3.0 (2H, m), 3.2 (2H, m), 3.5 (4H, m), 4.0 (2H, m), 4.6 (2H, m), 5.0 (1H, m), 7.3–7.5 (8H, m, aromatic). Mass: M+1=441

Preparation 30

Synthesis of (S)-N-[3-[3-fluoro-4-[4-(cyclobutanoyl)piperazinyl-1-yl]phenyl]-2-oxooxazolidin-5-ylmethyl]acetamide

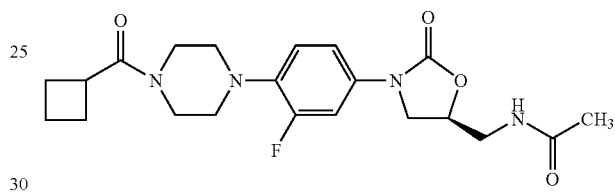

3-Fluoro-4-[piperazinyl-4-yl]phenyl]-2-oxazolidin-5-yl]methyl]acetamide (200 mg, 0.47 mmol) (obtained according to the procedure described in preparation 9) was reacted with cyclobutane carbonyl chloride (49 μl, 0.6 mmol) and K$_2$CO$_3$ (190 Mg, 1.4 mmol) in DMF (10 ml) at the ambient temperature for 12 hrs. The product was purified through a silica gel column using 10% MeOH in EtOAc to obtain the title compound (150 mg, yield 72 %).

$^1$H-NMR (CDCl$_3$): δ 0.8 (3H, m), 1.3 (3H, m), 2.0 (3H, s), 2.9 (4H, m), 3.8 (3H, m), 4.0 (2H, m), 4.1 (2H, m), 4.4 (1H, m), 4.5 (2H, m), 6.9–7.5 (3H, m, aromatic). Mass: M+1=419

The following compounds were prepared according to the procedure given in preparation 30.

| Preparation No. | Structure | Analytical Data |
|---|---|---|
| 31 | ![structure] | $^1$H-NMR (CDCl$_3$): δ 1.0(3H, m), 1.8(4H, m), 2.0(2H, m), 2.1(3H, m), 3.0(4H, m), 3.8(1H, m), 4.0(4H, m), 4.3(1H, m), 4.5(2H, m), 5.0(1H, m), 6.9–7.4(3H, m, aromatic). Mass = 433, M + 1 |

Preparation 32

Synthesis of (S)-N-[3-[3-fluoro-4-[4-(N-t-butoxy-carbonylpyrrolidin-2-ylcarbonyl)piperazin-1-yl]phenyl]-2-oxooxazolidin-5-ylmethyl]acetamide

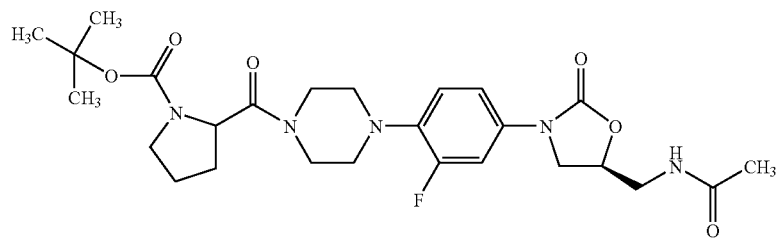

3-Fluoro-4-[piperazinyl-4-yl]phenyl]-2-oxazolidin-5-yl] methyl]acetamide (5.0 g, 14.88 mmole) (obtained according to the procedure described in preparation 9) was dissolved in dimethylformamide (50 ml). To this, N-(tert-butoxycarbonyl)-L-proline (3.51 g, 16.36 mmole), 1-hydroxybenztriazole hydrate (2.41 g, 17.85 mmole) and 4-dimethylamino pyridine (1.81 g, 14.88 mmole) was added and stirred for 15 minutes. 1-(3-Dimethylaminopropyl)-3-ethyl-carbodiimide hydrochloride (7.1 g, 37.2 mmole) was added to above reaction mixture and stirred for 2 hours at ambient tempera ture. After completion of reaction, the reaction mixturewas poured on to water (300 ml) and extracted with dichloromethane. The organic layer was dried over anhydrous sodium sulphate and concentrated to give crude product which was purified by column chromatography using silicagel as absorbent (2% methanol in ethyl acetate) to afford the title compound (5.42 g, 70.3%, purity 98.91%).

$^1$HNMR (CDCl$_3$, 400 MHZ): δ 1.46 (9H, s), 1.89–2.02 (3H, m), 2.09 (3H, s), 2.21 (1H, m), 3.04 (4H, s), 3.4–3.9 (9H, m), 4.02 (1H, t), 4.66 (1H, dd), 4.76 (1H, m), 6.05 (1H, s), 6.91 (1H, t), 7.08 (1H, t), 7.54 (1H, dd). Mass: M+1=533

The following compounds were prepared according to the procedure given in preparation 32.

| Preparation No. | Structure | Analytical Data |
|---|---|---|
| 33 | ![structure] | Mass: M + 1 = 494 |

Preparation 34

Synthesis of (S)-N-[3-[3-fluoro-4 [(N-t-butoxycarbonylpyrrolidin-2-ylthiocarbonyl)piperazin-1-yl]phenyl]-2-oxooxazolidin-5-ylmethyl]thioacetamide

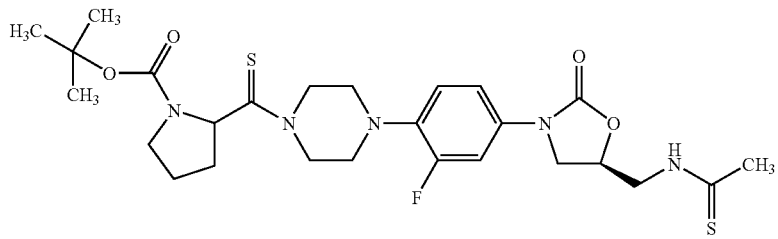

(S)-N-[3-[3-Fluoro-4-[4-(N-t-butoxycarbonylpyrrolidin-2-ylcarbonyl)piperazin-1-yl]phenyl]-2-oxooxazolidin-5-ylmethyl]acetamide (1.1 g, 2.06 mmole) (prepared according to the procedure described in preparation 32) was dissolved in tetrahydrofuran (20 ml). To this, Lawesson's reagent (1.74 g, 4.3 mmole) was added and stirred at 70–75° C. for 20 hours. After completion of reaction, the reaction mixture was diluted with ethyl acetate and washed with water. The organic layer was dried over anhydrous sodium sulphate and concentrated to give the crude product which was purified by column chromatography using silica gel to afford the title compound (450 mg, 38.59%). Mass: M+1=567.

The following compounds were prepared according to the procedure given in preparation 34.

(S)-N-[3-[3-fluoro-4-[N-t-butoxycarbonylpiperazin-1-yl]phenyl]-2-oxooxazolidin-5-ylmethyl]azide (1.7 gm, 4.0476 mmol) (obtained according to the procedure described in preparation 7) was treated with 50% TFA/DCM (10 ml) for 4 hrs. After evaporation of excess solvent, the product was treated with Et₃N (13 ml) in DCM (15 ml). The solvent was evaporated under reduced pressure, the residue was taken into dioxane (25 ml). 5—Nitro furoic acid (642 mg, 4 mmol) was treated with NHS (617 mg, 5.4 mmol), DCC (925 mg, 4.5 mmol) and DMAP (700 mg, 5.8 mmol) and the mixture was allowed to react for 4 hrs. The precipitate was filtered

| Preparation No. | Structure | Analytical Data |
|---|---|---|
| 35 | 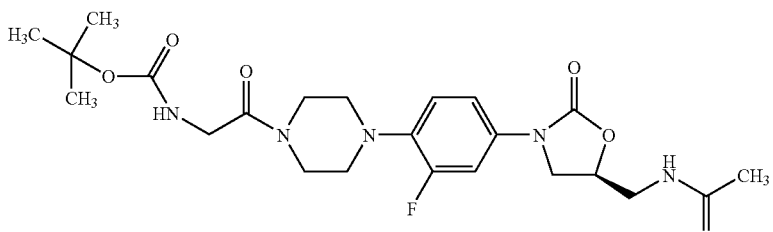 | Mass: M + 1 = 526 |

Preparation 36

Synthesis of (S)-N-[3-[3-fluoro-4-[4(furan-3-ylthiocarbonyl)piperazin-1-yl]phenyl]-2-oxooxazolidin-5-ylmethyl]azide

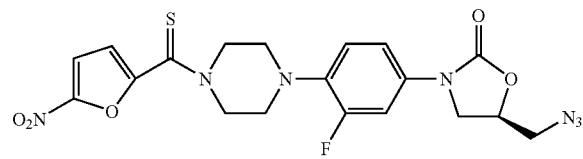

Step (i)

Synthesis of (S)-N-[3-[3-fluoro-4–14-(furan-3-ylthiocarbonyl)piperazin-1-yl]phenyl]-2-oxooxazolidin-5-ylmethyl]azide

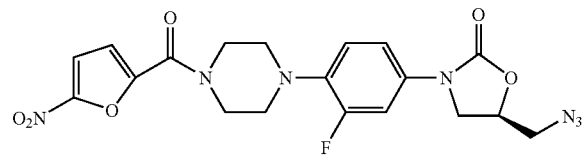

and the filtrate was added to the amine in dioxane. The reaction was allowed overnight and the amide was extracted with EtOAc and water, the organic phase separated and purified over column chromatography to afford the title compound.

Step (ii)

Synthesis of (S)-N-[3-[3-fluoro-4-[4-(furan-3-ylthiocarbonyl)piperazin-1-yl]phenyl]-2-oxooxazolidin-5-ylmethyl]azide To a solution of (S)-N-[3-[3-fluoro-4-[4-(firan-3-ylthiocarbonyl)piperazin-1-yl]phenyl]-2-oxooxazolidin-5-ylmethyl]azide (300 mg, 0.65 mmol) dissolved in toluene (50 ml) Lawesson's reagent (415 mg, 1 mmol) was added and heated to 80° C. for 4 hrs. The product was purified using column chromatography to obtain the title compound (108 mg).

The following compounds were prepared according to the procedure given in 10 preparation 36.

| Preparation No. | Structure | Analytical Data |
|---|---|---|
| 37 | 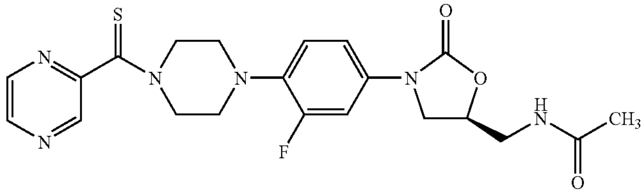 | ¹HNMR (DMSO-d₆, 400 MHz): δ 2.5(3H, s), 3.0(4H, m), 3.6(2H, m), 3.7(4H, m), 4.5(2H, m), 4.9(1H, m), 6.8–8.1(6H, m, aromatic) Mass: M + 1 = 459. |
| 38 | 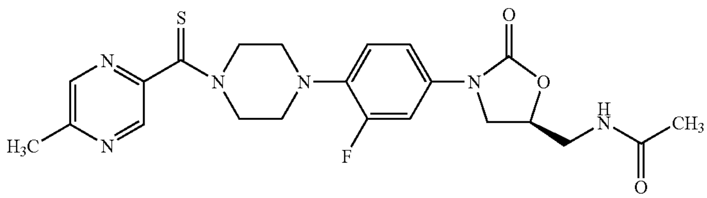 | ¹HNMR (CDCl₃, 400 MHz): δ 1.3(3H, s), 2.5(3H, s), 3.0(4H, m), 3.7(2H, m), 3.8(4H, m), 4.05(2H, m), 5.0(1H, m), 6.8–7.4(5H, m aromatic). Mass: M + 1 = 473 |

Preparation 39

Synthesis of (S)-N-[3-[3-fluoro-4-[4-(N-t-butoxycarbonylaminothioacetyl)piperazin-1-yl]phenyl]-2-oxooxazolidin-5-ylmethyl]acetamide

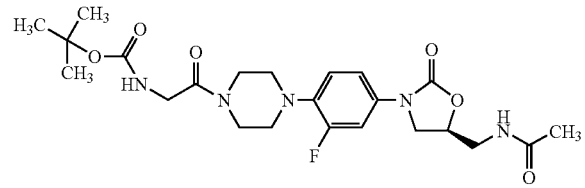

Step (i)

Synthesis of (S)-N-[3-[3-fluoro-4-[4-(N-t-butoxycarbonylaminoacetyl)piperazin-1-yl]phenyl]-2-oxooxazolidin-5-ylmethyl]azide

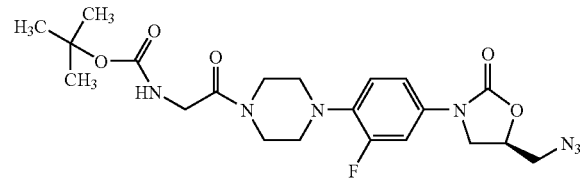

To a solution of (S)-N-[3-[3-fluoro-4-[piperazin-1-yl]phenyl]-2-oxooxazolidin-5-ylmethyl]azide (2 g, 6.25 mmole) dissolved in dichloromethane (50 ml), N-(t-butoxycarbonyl) glycine (1.2 g, 6.87 mmole), 1-hydroxybenztriazole hydrate (1.01 mg, 7.5 mmole) and 4-dimethylamino pyridine (0.76 g, 6.25 mmole) was added and stirred for 15 minutes. 1-(3-Dimethylaminopropyl)-3-ethyl-carbodiimide hydrochloride (2.98 g, 15.6 mmole) was added to above reaction mixture and stirred for 3 hours at ambient temperature. After completion of reaction, the reaction mixture was washed with water, dried and concentrated to give the title compound (1.85 g, 62.08%).

Mass: M+1=478 ¹HNMR(CDCl₃, 400MHz): δ 1.47 (9H, s), 3.03 (4H, q), 3.56 (2H, m), 3.60 (1H, d), 3.69 (1H, dd), 3.82 (3H, m), 4.03 (3H, m), 4.78 (1H, m), 5.52 (1H, bs), 6.92 (1H, t), 7.11 (1H, dd), 7.49 (1H, dd).

Step (ii)

Synthesis of (S)-N-[3-[3-fluoro-4-[4(N-t-butoxycarbonylaminothioacetyl)piperazin-1-yl]phenyl]-2-oxooxazolidin-5-ylmethyl]azide

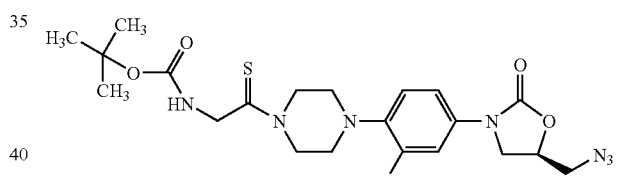

To a solution of (S)-N-[3-[3-fluoro-4-[4-(N-t-butoxycarbonylaminoacetyl)piperazin-1-yl]phenyl]-2-oxooxazolidin-5-ylmethyl]azide (1.0 g, 2.09 mmole) dissolved in tetrahydrofuran (10 ml), Lawesson's reagent (0.804 mg, 2 mmole) was added and stirred at 70–75° C. for 4 hours. After completion of the reaction, the reaction mixture was diluted with water and extracted with ethyl acetate. The organic layer was dried over anhydrous sodium sulfate and concentrated to give crude product, which was purified by column chromatography to yield the title compound (256 mg, 24.7 %).

Mass: M+1=494

Step (iii)

Synthesis of (S)-N-[3-[3-fluoro-4-[4-(N-t-butoxycarbonylaminothioacetyl)piperazin-1-yl]phenyl]-2-oxooxazolidin-5-ylmethyl]acetamide (S)-N-[3-[3-fluoro-4-[4-(N-t-butoxycarbonylaminothioacetyl)piperazin-1-yl]phenyl]-2-oxooxazolidin-5-ylmethyl] azide (100 mg, 0.202 mmole) and thioacetic acid (0.4 ml) was stirred at ambient temperature for 20 hrs. After completion of reaction, the reaction mixture was diluted with dichloromethane (10 ml) and purified by preparative TLC to yield the title compound (55 mg, 53.4%). Mass: M+1=510

¹HNMR(CDCl₃, 400MHz): δ 1.46 (9H, s), 2.03 (3H, s), 3.16 (4H, m), 3.73 (3H, m), 3.93 (2H, m), 4.02 (1H, t), 4.16 (2H, s), 4.49 (2H, t), 4.76 (1H, m), 5.96 (1H, t), 6.90 (1H, t), 7.07 (1H, dd), 7.50 (1H, dd).

EXAMPLE 1

Synthesis of (S)-N-[3-[3-fluoro-4-[4(thiophen-3-ylthiocarbonyl)piperazin-1-yl]phenyl]-2-oxooxazolidin-5-ylmethyl]thioacetamide

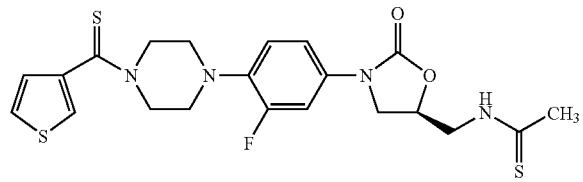

To a solution of (S)-N-[3-[3-fluoro-4-[4-(thiophen-3-ylcarbonyl)piperazin-1-yl]phenyl]-2-oxooxazolidin-5-ylmethyl] acetamide (150 mg, 0.34 mmol) (obtained according to the procedure described in preparation 10) in dry toluene (10 ml) Lawesson's reagent (203 mg, 0.34 mmol) was added. The mixture was stirred initially at room temperature for 1 hr and then heated at 110–120° C. for 4–5 hrs. The reaction mixture was extracted with EtOAc (2×200ml) and water (50 ml). The organic layer was separated, dried over Na₂SO₄ and solvent evaporated under reduced pressure and purified through a silica gel column using 50% EtOAc in hexane as eluent to afford the title compound (130 mg, yield 81%).

¹H-NMR (CDCl₃): δ 2.5 (3H, s), 3.0 (4H, m), 3.9 (1H, m), 4.0 (4H, m), 4.29 (1H, m), 4.5 (2H, m), 5.0 (1H, m), 6.9–7.8 (6H, m, aromatic). Mass: M+1=479

The following compounds were prepared according to the procedure given in example 1.

| Example No. | Structure | Analytical Data |
| --- | --- | --- |
| 2 | 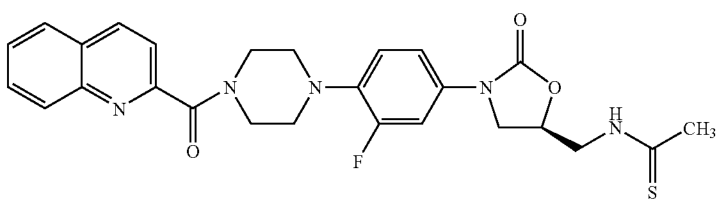 | ¹H-NMR (CDCl₃): δ 2.6(3H, s), 3.3(4H, m), 4.0(3H, m), 4.2(1H, m), 4.5(2H, m), 4.6(2H, m), 5.0(1H, m), 6.9–8.1 (9H, m, aromatic). Mass: M + 1 = 524. |
| 3 | 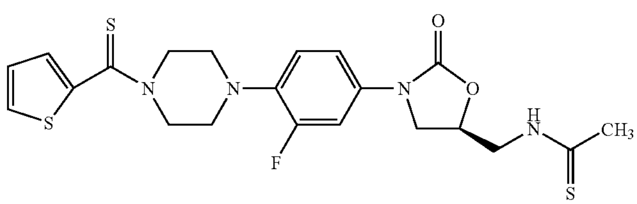 | ¹H-NMR (CDCl₃): δ 2.6(3H, s), 3.1(4H, m), 3.8(1H, m), 3.4.(3H, m), 4.3(2H, m), 4.5(2H, m), 4.9(1H, m), 6.9–7.7(6H, m, aromatic). Mass: M + 1 = 479. |
| 4 | 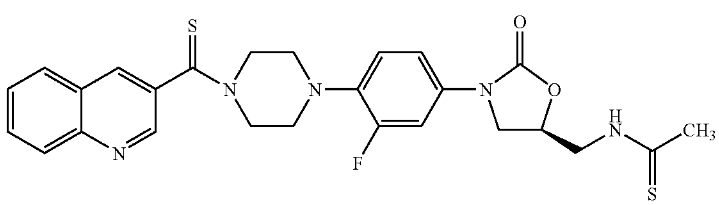 | ¹H-NMR (CDCl₃): δ 2.6(3H, s), 3.1(4H, m), 3.3(2H, m), 4.0(3H, m), 4.1(2H, m), 4.2(1H, m), 4.6 (2H, m), 5.0(1H, m), 6.9–8.2 (9H, m, aromatic). Mass: M + 1 = 524. |
| 5 | 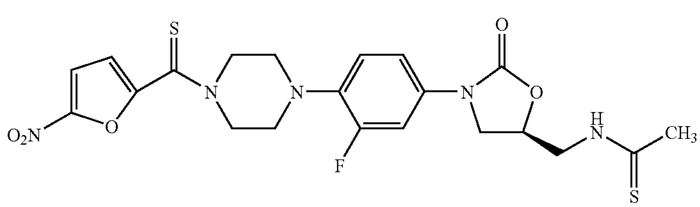 | ¹H-NMR (CDCl₃): δ 2.6(3H, s), 3.2(4H, m), 4.0(2H, m), 4.1(4H, m), 4.4(2H, m), 5.0(1H, m), 6.9–7.5 (5H, m, aromatic). Mass: M + 1 = 508. |
| 6 | 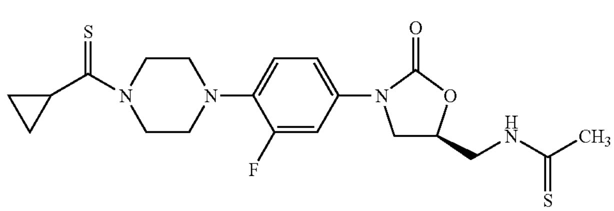 | ¹H-NMR (CDCl₃): δ 1.1(2H, m), 1.4(2H, m), 2.0(1H, m), 2.6(3H, s), 3.2(4H, m), 3.7(1H, m), 3.8 (4H, m), 4.3(1H, m), 4.6(2H, m), 4.9(1H, m), 7.0–7.7(3H, m, aromatic). Mass: M + 1 = 437. |

| Example No. | Structure | Analytical Data |
|---|---|---|
| 7 | 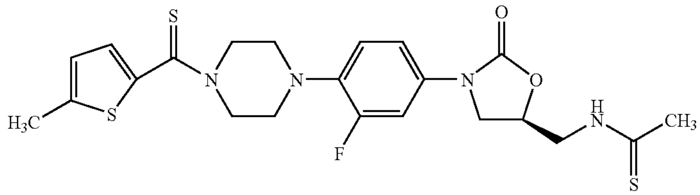 | $^1$H-NMR (CDCl$_3$): δ 2.5(3H, s), 2.6(3H, s), 3.1(4H, m), 3.8(1H, m), 4.1 (3H, m), 4.3(4H, m), 5.0 (1H, m), 6.6–7.7(5H, m, aromatic). Mass: M + 1 = 493. |
| 8 | 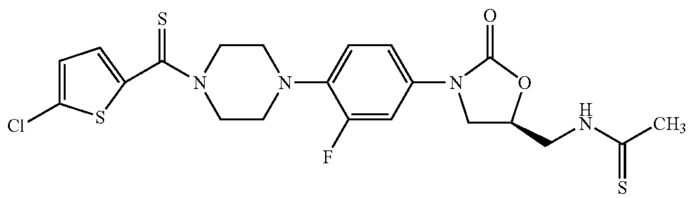 | $^1$H-NMR (CDCl$_3$): δ 2.6(3H, s), 3.2(4H, m), 3.9(1H, m), 4.0(3H, m), 4.4(4H, m), 5.0(1H, m), 6.8–7.9(5H, m, aromatic). Mass: M + 1 = 513. |
| 9 | 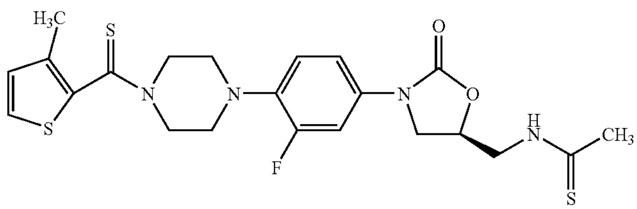 | $^1$H-NMR (CDCl$_3$): δ 2.2(3H, s), 2.7(3H, m), 3.1(4H, m), 4.0(2H, m), 4.1 (4H, m), 4.3(1H, m), 4.5 (1H, m), 5.0(1H, m), 6.7–7.5(5H, m, aromatic). Mass: M + 1 = 493. |
| 10 | 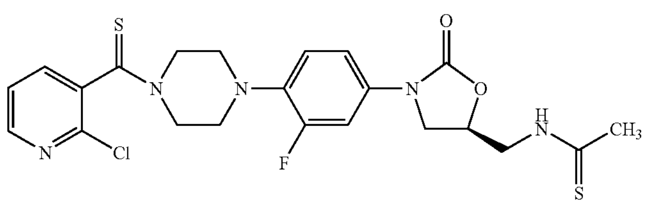 | $^1$H-NMR (CDCl$_3$): δ 2.6(3H, s), 3.2(2H, m), 3.3(2H, m), 3.8(2H, m), 4.0 (4H, m), 4.1(1H, m), 4.5 (1H, m), 5.3(1H, m), 6.7–8.3(6H, m, aromatic). Mass: M + 1 = 508. |
| 11 | 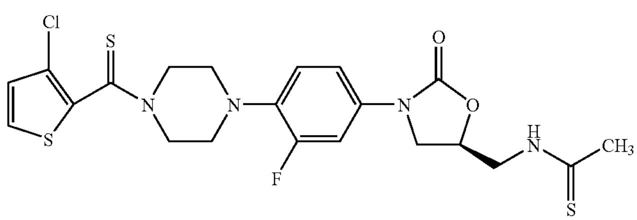 | $^1$H-NMR (CDCl$_3$): δ 2.5(3H, s), 3.1(4H, m), 3.5(1H, m), 4.0(3H, m), 4.2(4H, m), 5.0(1H, m), 6.8–7.8(5H, m, aromatic). 7.8(5H, m, aromatic). Mass: M + 1 = 513. |
| 12 | 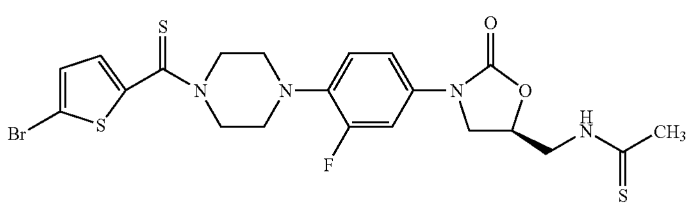 | $^1$H-NMR (CDCl$_3$): δ 2.6(3H, s), 3.1(4H, m), 3.9(2H, m), 4.1(2H, m), 4.4(4H, m), 5.0(1H, m), 6.8–7.5(5H, m, aromatic). Mass: M + 1 = 558. |
| 13 | 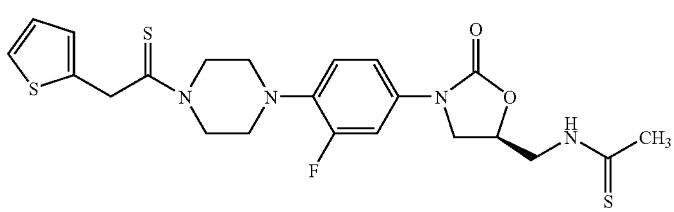 | $^1$H-NMR (CDCl$_3$): δ 2.5(3H, s), 2.8(2H, m), 3.1(2H, m), 3.8(3H, m), 4.0(2H, m), 4.4(1H, m), 4.5 (4H, m), 5.0(1H, m), 6.8–7.9(6H, m, aromatic). Mass: M + 1 = 493. |

-continued

| Example No. | Structure | Analytical Data |
|---|---|---|
| 14 | 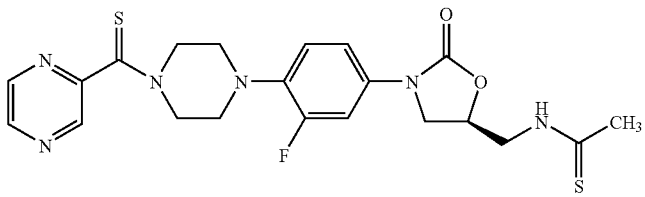 | ¹H-NMR (CDCl₃): δ 2.5(3H, s), 3.2(4H, m), 3.7(4H, m), 4.0(2H, m), 4.6(2H, m), 4.9(1H, m), 6.9–8.0(6H, m, aromatic). Mass: M + 1 = 475. |
| 15 | 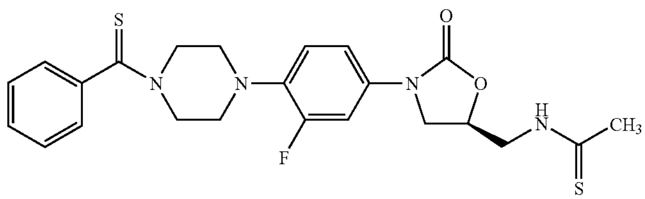 | ¹H-NMR (CDCl₃): δ 2.5(3H, s), 3.0(2H, m), 3.2(2H, m), 3.8(4H, m), 4.1(2H, m), 4.6(2H, m), 5.0 (1H, m), 6.9–7.7 (8H, m, aromatic). Mass: M + 1 = 473. |
| 16 | 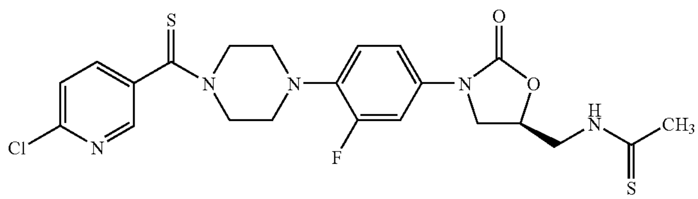 | ¹H-NMR (CDCl₃): δ 2.6(3H, s), 3.1(4H, m), 3.8(2H, m), 4.0(5H, m), 4.6(1H, m), 5.0(1H, m), 6.7–8.3 (6H, m, aromatic). Mass: M + 1 = 508. |
| 17 | 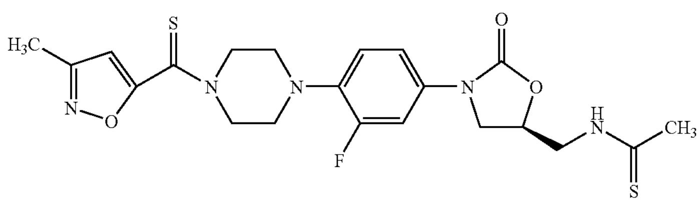 | ¹H-NMR (CDCl₃): δ 2.3(3H, s), 2.5(3H, s), 3.2(4H, m), 3.7(3H, m), 4.0(2H, m), 4.4(1H, m), 4.6 (2H, m), 5.0(1H, m), 7.0–8.2(4H, m, aromatic). Mass: M + 1 = 478. |
| 18 | 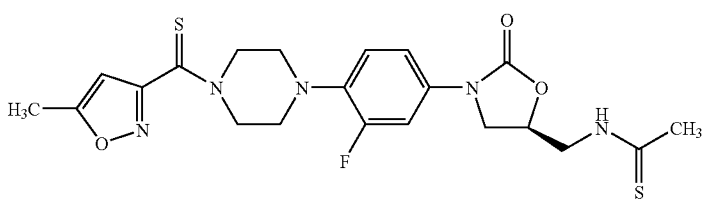 | ¹H-NMR (CDCl₃): δ 2.3(3H, s), 2.6(3H, s), 3.2(4H, m), 3.8(3H, m), 4.0(2H, m), 4.4(1H, m), 4.5 (2H, m), 5.0(1H, m), 7.0–8.4(4H, m, aromatic). Mass: M + 1 = 478. |
| 19 | 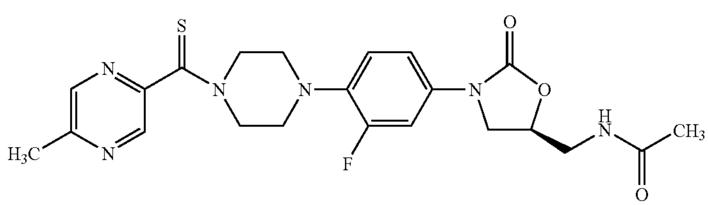 | ¹H-NMR (CDCl₃): δ 2.5(3H, s), 2.6(3H, s), 3.2(4H, m), 3.7(4H, m), 4.1(2H, m), 4.6(2H, m), 5.0 (1H, m), 6.9–8.0(5H, m, aromatic). Mass: M + 1 = 489. |
| 20 | 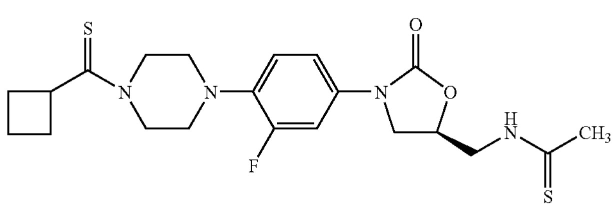 | ¹H-NMR (CDCl₃): δ 0.8(3H, m), 1.3(3H, m), 2.6(3H, s), 3.0(4H, m), 3.8(3H, m), 4.0(2H, m), 4.1 (2H, m), 4.4(1H, m), 4.5(2H, m), 6.9–7.8(3H, m, aromatic). Mass: M + 1 = 451. |

| Example No. | Structure | Analytical Data |
|---|---|---|
| 21 | 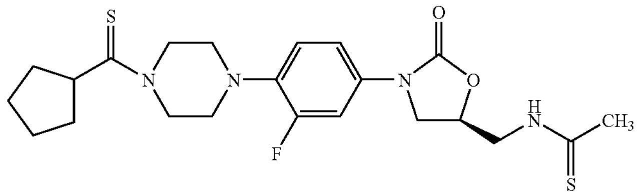 | $^1$H-NMR (CDCl$_3$): δ 1.0(3H, m), 1.8(4H, m), 2.0(2H, m), 2.6(3H, m), 3.1 (4H, m), 3.8(1H, m), 4.1 (4H, m), 4.3(1H, m), 4.6(2H, m), 4.9(1H, m), 6.9–7.9(3H, m, aromatic). Mass: M + 1 = 465. |
| 22 | mp: 177–179° C. | $^1$HNMR (CDCl$_3$, 400 MHZ): δ 2.62(3H, s), 3.26(4H, m), 3.8(1H, q), 4.07(2H, m), 4.28(1H, m), 4.61(2H, t), 4.96(1H, m), 5.05(2H, t), 6.96(1H, t), 7.06(1H, d), 7.26(2H, m), 7.48(1H, dd), 7.9(1H, t) 10.6(1H, s). Mass: M + 1 = 463 |

EXAMPLE 23

Synthesis of (S)-N-[3-[3-fluoro-4-[4-(pyrrolidin-2-ylthiocarbonyl)piperazin-1-yl]phenyl]-2-oxooxazolidin-5-ylmethyl]thioacetamide hydrochloride $^1$HNMR (CDCl$_3$, 400 MHz): δ 1.86 (1H, m), 2.13 (2H, m), 2.49 (3H, s), 2.65 (1H, m), 3.22 (4H, m), 3.39 (1H, m), 3.55 (1H, m), 3.9 (1H, t), 4.03 (4H, m), 4.14 (1H, t), 4.48 (2H, q), 4.82 (1H, t), 5.1 (1H, m), 7.08 (1H, t), 7.21 (1H, dd) 7.55 (1H, dd). M/Z$^{m+1}$: 467

The following compounds were prepared according to the procedure given in example 23.

| Example No. | Structure | Analytical Data |
|---|---|---|
| 24 | mp: 182-184 ° C. | $^1$HNMR (DMSO-d$_6$, 400 MHz): δ 2.49(3H s), 3.11(4H s), 3.81(1H, t), 3.9(4H, t), 4.07(2H, s), 4.13(1H, t), 4.36(2H, s), 4.9(1H, m,) 7.10(1H, t), 7.22(1H, dd), 7.54(1H, dd), 8.31(2H, s). Mass; M + 1 = 426. |

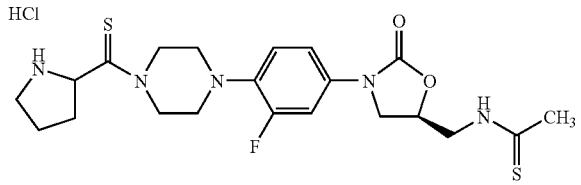

(S)-N-[3-[3-fluoro-4-[4-(N-t-butoxycarbonylpyrrolidin-2-ylcarbonyl)piperazin-1-yl]phenyl]-2-oxooxazolidin-5-ylmethyl]acetamide (210 mg, 0.371 mmole) (prepared according to the procedure described in preparation 34) was dissolved in tetrahydrofuran (4 ml). To this, 4 N HCl (1 ml) in tetrahydrofuran at 0° C. was added and stirred for 1 hour. After completion of reaction, the reaction mixture was concentrated and purified by preparative HPLC to obtain the title compound (93 mg, 54%, purity 97.6%).

EXAMPLE 25

Synthesis of (S)-N-[3-[3-fluoro-4-[4-(furan-3-ylthiocarbonyl)piperazin-1-yl]phenyl]-2-oxooxazolidin-5-ylmethyl]acetamide

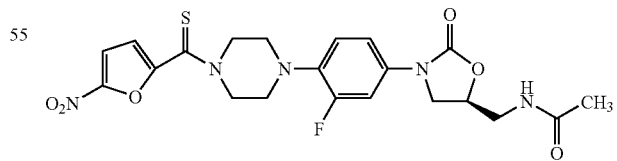

(S)-N-[3-[3-fluoro-4-[4-(furan-3-ylthiocarbonyl)piperazin-1-yl]phenyl]-2-oxooxazolidin-5-ylmethyl]azide obtained in step (ii) was then treated with neat thio acetic acid (1.2 ml) for 5 hrs and extracted with EtOAc/water, and purified using column chromatography to afford the title compound (95.24, 50%, purity 95.24)

¹HNMR(DMSO-d₆, 400 MHz): δ 1.8 (3H, s), 3.1 (2H, t), 3.2 (2H, t), 3.87 (2H, m), 3.7 (1H, m), 4.00 (2H, t), 4.06 (1H, t), 4.4 (2H, t), 4.7 (H, m), 7.1–8.2 (3H, m, aromatic). Mass: M+1=492

The following compounds were prepared according to the procedure given in example 25.

A solution of (S)-N-[3-[3-fluoro-4-[4-(N-t-butoxycarbonylaminothioacetyl)piperazin-1-yl]phenyl]-2-oxooxazolidin-5-ylmethyl]acetamide (70 mg; 0.137 mmole) dissolved in dicholomethane (10 ml) was bubbled dry HCl gas at 0° C. for 5 minutes and the reaction mixture was stirred at same temperature for 40 minutes. After completion of reaction,

| Example No. | Structure | Analytical Data |
|---|---|---|
| 26 | 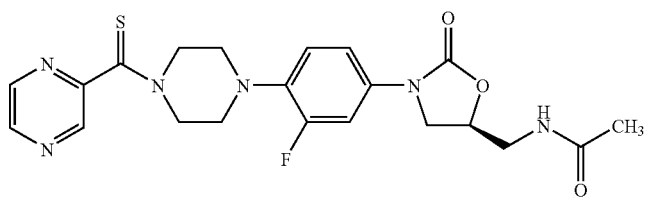 | ¹HNMR (DMSO-d₆, 400 MHz): δ 2.5(3H, s), 3.0(4H, m), 3.6(2H, m), 3.7(4H, m), 4.5(2H, m), 4.9 (1H, m), 6.8–8.1(6H, m, aromatic) Mass: M + 1 = 459. |
| 27 | 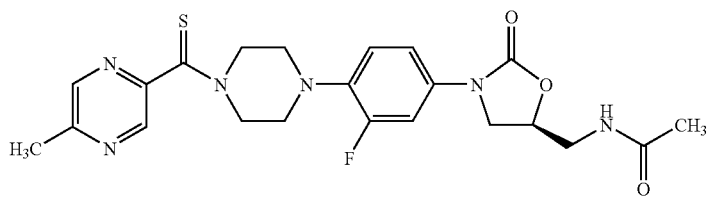 | ¹HNMR (CDCl₃, 400 MHz): δ 1.3(3H, s), 2.5(3H, s), 3.0(4H, m), 3.7(2H, m), 3.8(4H, m), 4.05(2H, m), 5.0(1H, m), 6.8–7.4(5H, m aromatic). Mass: M + 1 = 473 |

EXAMPLE 28

(S)-N-[3-[3-fluoro-4-[4-(aminothioacetyl)piperazin-1-yl]phenyl]-2-oxooxazolidin-5-ylmethyl]acetamide

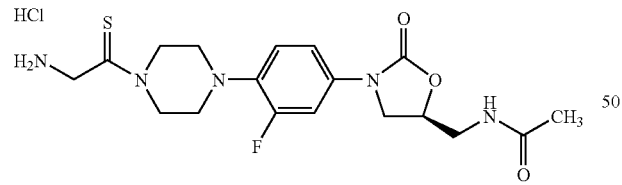

the reaction mixture was concentrated to give the title compound (59 mg, 96.7 %), mp: 202–204° C. Mass: M+1=410. ¹HNMR(DMSO-d₆, 400MHz): δ 1.82 (3H, s), 3.10 (4H, bs), 3.55 (3H, m), 3.89 (3H, m), 4.06 (3H, bs), 4.35 (2H, bs), 4.70 (1H, m), 7.09 (1H, t), 7.18 (1H, dd), 7.52 (1H, dd), 8.29 (3H, m).

EXAMPLE 29

Synthesis of (S)-N-[3-[3-fluoro-4-(4-(N,N'-dimethylaminophenyl)thiocarbamidopiperazin-1-yl)phenyl]-2-oxooxazolidin-5methyl]acetamide

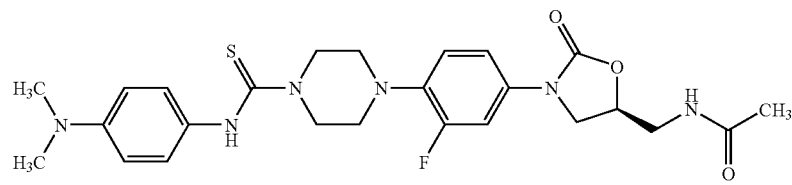

To a solution of 3-{4-[4-(benzyloxycarbonyl)piperazine-1-yl]-3-fluorophenyl}-2-oxooxazolidin-5-methylacetamide (111 mg, 0.236 mmol) dissolved in methanol (10 ml), 10% Pd/c (50 mg) and ammonium formate (120 mg, 1.9047 mmol) was added and refluxed for 2 hrs. The reaction mixture was filtered off and the filtrate was evaporated under reduced pressure. The residue obtained was dissolved in methanol (10 ml) and NaOH (33 mg, 0.82 mmol) was added and cooled to 4° C., and 4-(N,N'-dimethylamino)phenyl-isothiocyante (86.5 mg, 0.48 mmol) was added and allowed to stir overnight. The precipitate formed was filtered off washed with methanol to afford pure the title compound as off white solid (22.63 mg).

$^1$H-NMR (DMSO): δ 1.83 (3H, s), 2.87 (6H, s), 3.02 (4H, t), 3.39 (2H, t), 3.54 (1H, t), 4.02 (5H, m), 4.55 (1H, m), 6.6–7.5 (7H, m aromatic). Mass: M+1=515

The following compounds were prepared according to the procedure given in example 29.

| Example No. | Structure | Analytical Data |
|---|---|---|
| 30 | 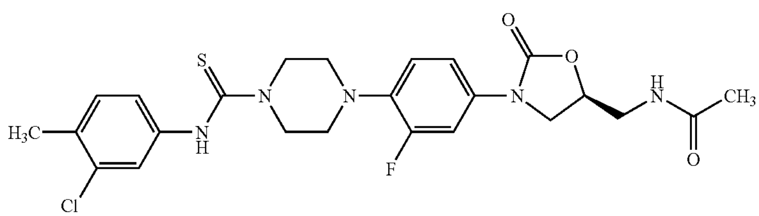 | $^1$H-NMR (DMSO): δ 1.85(3H, s), 2.29(3H, s), 3.04(3H, t), 3.4(2H, t), 3.7(2H, t), 4.05(5H, m), 4.72(1H, m), 7.1(6H, m aromatic). Mass: M + 1 = 520 |
| 31 | 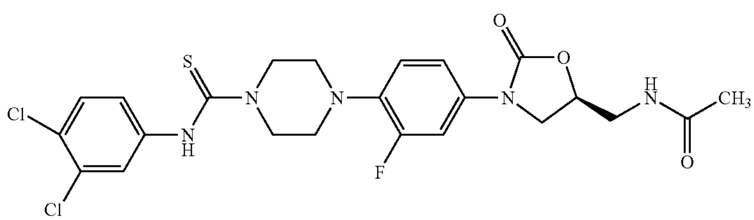 | $^1$H-NMR (DMSO): δ 1.85(3H, s), 3.05(4H, t), 3.07(4H, t), 3.4(2H, t), 3.71(1H, t), 4.07(5H, t), 4.55(1H, m), 7.1–7.55(6H, m, aromatic). Mass: M + 1 = 540 |
| 32 | 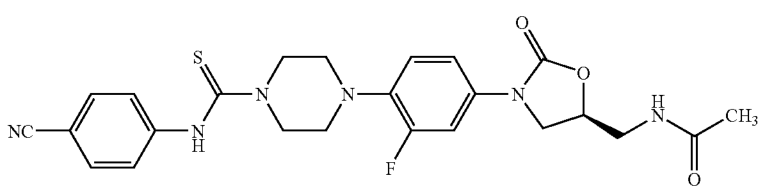 | $^1$H-NMR (DMSO): δ 1.82(3H, s), 3.04(4H, t), 3.39(2H, t), 3.7(1H, t), 4.0(5H, m), 4.71(1H, m), 7.09 (7H, m aromatic). Mass: M + 1 = 497 |
| 33 | 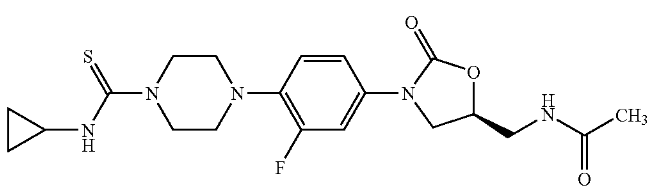 | $^1$H-NMR (DMSO): δ 0.5(2H, q), 0.65(2H, q), 1.82(3H, s), 2.9(5H, m), 3.3(2H, t), 3.67(1H, t), 3.88(3H, t), 4.0(1H, t), 4.68(1H, m), 7.06–7.7(3H, m aromatic). Mass: M + 1 = 436 |
| 34 | 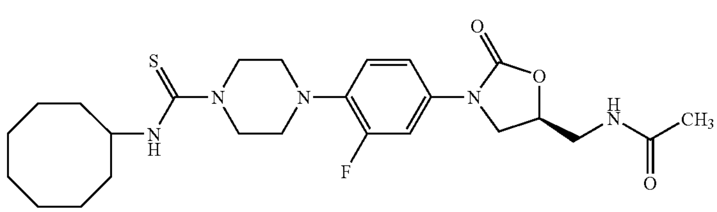 | $^1$H-NMR (DMSO): δ 1.5(8H, m), 1.64(6H, m), 1.85(3H, m), 2.95(4H, t), 3.4(2H, t), 3.69(1H, t), 3.8(4H, t), 4.08(1H, t), 4.5(1H, m), 4.6(1H, m), 7.06–7.7(3H, m aromatic). Mass: M + 1 = 506 |
| 35 | 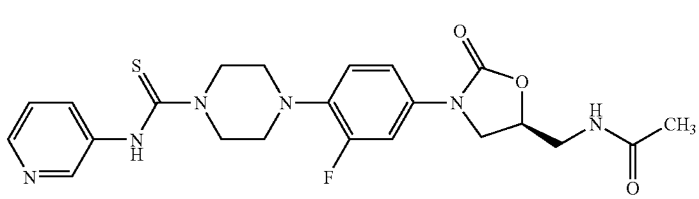 | $^1$H-NMR (DMSO): δ 1.8(3H, s), 3.07(4H, t), 3.38(2H, t), 3.68(1H, t), 4.06(5H, t), 4.7(1H, m), 7.12–8.48 (7H, m aromatic). Mass: M + 1 = 473 |

| Example No. | Structure | Analytical Data |
|---|---|---|
| 36 | 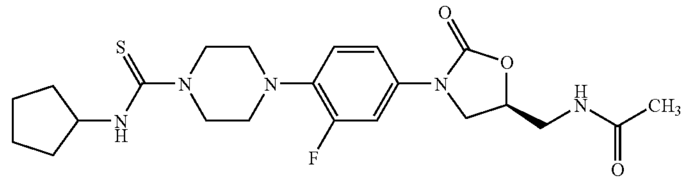 | $^1$H-NMR (DMSO): δ 1.48(4H, m), 1.65(2H, m), 1.82(3H, s), 1.9(2H, m), 2.9(4H, t), 3.38(2H, t), 3.69(1H, t), 3.9(4H, t), 4.08(1H, t), 4.6(1H, m), 4.7(1H, m), 7.08–7.51 (3H, m aromatic). Mass: M + 1 = 464 |
| 37 | 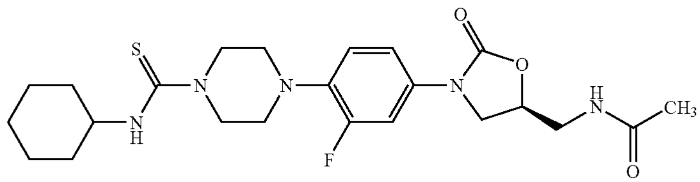 | $^1$H-NMR (DMSO): δ 1.09(1H, m), 1.24(4H, m), 1.5(1H, d), 1.7(2H, m), 1.86(5H, m), 2.95(4H, t), 3.39(2H, m), 3.67(1H, t), 3.9(4H, t), 4.06(1H, t), 4.2(1H, m), 4.7(1H, m), 7.06–8.25(3H, m aromatic). Mass: M + 1 = 477 |

EXAMPLE 38

(S)-N-[3-[3-Fluoro-4-(4-(4-nitrophenyl)carbamidopiperazin-1-yl)phenyl]-2-oxooxazolidin-5-methyl]acetamide;

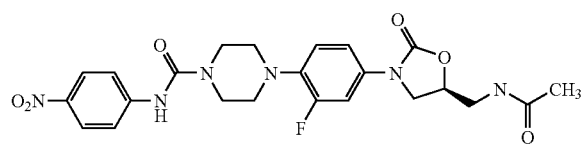

To a cold solution (4° C.) of 3-{4-[4(t-butoxycarbonyl)piperazinyl]-3-fluorophenyl}-2-oxooxazolidin-5-methylacetamide (200 mg, 0.458mmol) in dichloromethane (20 ml), 5% trifluoroacetic acid was added and stirred well for 4 hrs. The excess solvent and TFA were removed under vacuum, then added triethylamine (0.1 ml, 0.952 mmol) and 4-nitrophenylisocyante (105 mg, 0.64 mmol) in DCM (20 ml). The reaction mixture was allowed to react for 4 hrs and extracted with ethylacetate and water. The organic phase was separated and evaporated under reduced pressure to afford the crude product which was purified by column chromatography using silica gel to afford the pure title compound as yellow solid (100 mg).

$^1$H-NMk (CDCl$_3$): δ 2.0 (3H, s), 3.1(4H, d), 3.5 (2H, m), 3.7 (5H, t), 4.0(1H, t), 4.7 (1H, s), 7.1–8.1 (7H, m aromatic) Mass: M+1=501

The following compounds were prepared according to the procedure given in example 38.

| Example No. | Structure | Analytical Data |
|---|---|---|
| 39 | 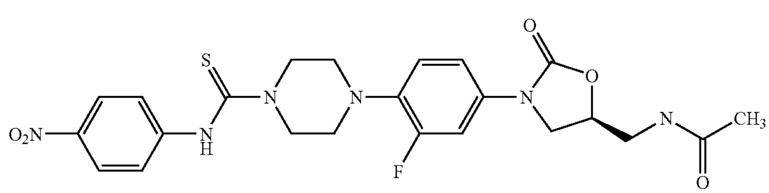 | $^1$H-NMR (CDCl$_3$): δ 2.0(3H, s), 2.1(1H, s), 2.9(1H, s), 3.0(1H, s), 3.2(4H, s), 3.3(2H, m), 3.7(1H, d), 3.8(1H, d), 4.0(1H, t), 4.7(1H, m), 7.1–8.1(7H, m aromatic) Mass: M + 1 = 516 |
| 40 | 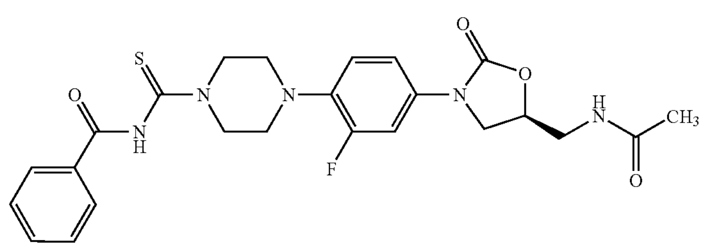 | $^1$H-NMR (CDCl$_3$): δ 2.0(3H, s), 3.2(4H, s), 3.5(2H, m), 3.7(1H, m), 3.8(2H, m), 4.0(1H, t), 4.6(2H, m), 4.9(1H, m), 7.0–7.9(8H, m aromatic) Mass: M + 1 = 500 |

| Example No. | Structure | Analytical Data |
|---|---|---|
| 41 | 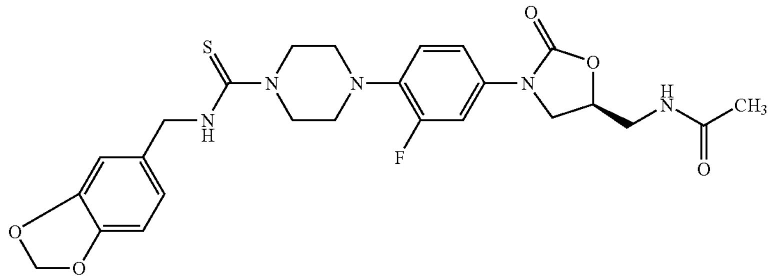 | ¹H-NMR (CDCl₃): δ 2.0(3H, s), 3.3(2H, s), 3.5(3H, m), 3.6(2H, s), 4.1(4H, t), 4.3(2H, s), 5.9(2H, m), 6.7–7.5(6H, m aromatic) Mass: M + 1 = 529 |
| 42 | 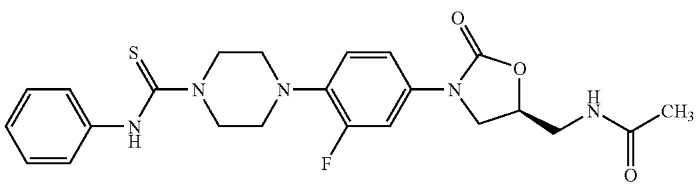 | ¹H-NMR (CDCl₃): δ 2.0(3H, s), 3.1(4H, t), 3.6(2H, m), 3.7(1H, m), 4.0(5H, m), 4.9(1H, m), 6.9–7.4(8H, m aromatic) Mass: M + 1 = 472 |
| 43 | 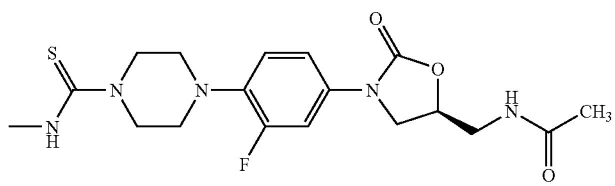 | ¹H-NMR (CDCl₃): δ 2.0(3H, s), 3.0(4H, s), 3.1(3H, d), 3.5(1H, t), 3.6(1H, t), 3.7(1H, d), 4.0(5H, s), 4.7(1H, s), 6.9–7.4(3H, m aromatic). Mass: M + 1 = 410 |
| 44 | 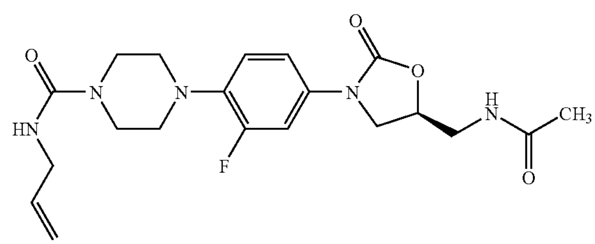 | ¹H-NMR (CDCl₃): δ 2.0(3H, s), 3.0(4H, t), 3.5(4H, t), 3.7(2H, t), 3.9(2H, m), 4.0(1H, t), 4.1(1H, s), 4.2(1H, s), 5.2(2H, m), 5.8(1H, t), 6.9–7.4(3H, m aromatic). Mass: M + 1 = 420 |

EXAMPLE 45

(S)-N-[3-[3-Fluoro-4-(4-(4-nitrophenyl)thiocarbamidopiperazin-1-yl)phenyl]-2-oxooxazolidin-5-methyl]thioacetamide;

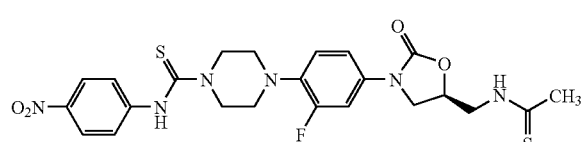

(S)-N-[3-[3-fluoro-4-[piperazin-1-yl]phenyl]-2-oxooxazolidin-5-ylmethyl]thioacetamide (100 mg, 0.285 mmol) was treated with 4-nitrophenylisothiocyante (60 mg, 0.399 mmol) in dichloromethane (20 ml). The reaction mixture was allowed to react for 4 hrs and extracted with ethylacetate and water. The organic phase was evaporated under reduced pressure to afford crude product which was purified by column chromatography using silica gel to afford pure title compound as yellow solid (44 mg).

¹H-NMR (CDCl₃): δ 2.5 (3H, s), 3.1 (4H, t), 3.4 (1H, m), 3.8 (1H, s), 4.1 (1H, m), 4.2 (4H, m), 4.3 (1H, d), 4.9 (1H, m), 6.9–8.1 (7H, m aromatic). Mass: M+1=533

The following compounds were prepared according to the procedure given in example 45.

| Example No. | Structure | Analytical Data |
|---|---|---|
| 46 | 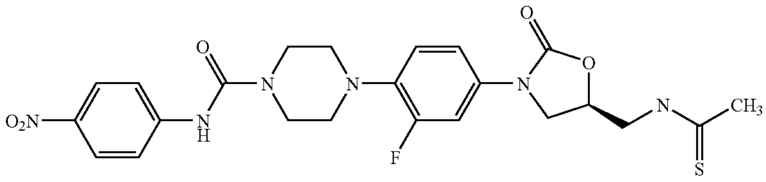 | ¹H-NMR (CDCl₃): δ 2.5(3H, s), 3.1(4H, t), 3.7(4H, t), 3.8(1H, m), 3.85(1H, m), 4.1(1H, d), 4.2(1H, d), 4.9(1H, m), 6.9–8.5(7H, m aromatic). Mass: M + 1 = 517 |
| 47 | 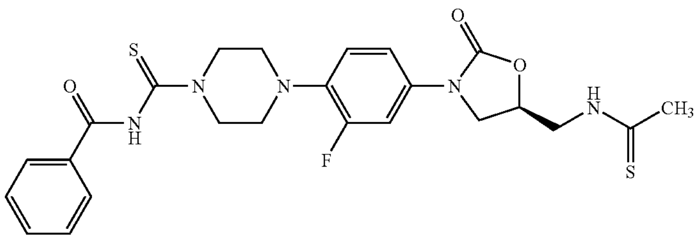 | ¹H-NMR (CDCl₃): δ 2.6(3H, s), 3.2(4H, s), 3.8(3H, m), 4.0(2H, m), 4.2(1H, m), 4.3(2H, s), 4.9(1H, m), 7.4–8.1(8H, m aromatic) Mass: M + 1 = 516 |
| 48 | 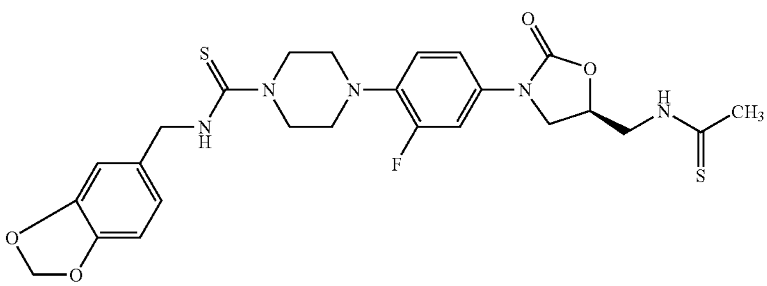 | ¹H-NMR (CDCl₃): δ 2.6(3H, s), 3.1(4H, t), 3.8(1H, d), 3.9(4H, t), 4.0(1H, d), 4.1(1H, d), 4.78(2H, d), 5.0(1H, m), d), 4.78(2H, d), 5.0(1H, m), 5.7(1H, s), 5.9(2H, s), 6.7–8.2(6H, m aromatic) Mass: M + 1 = 546 |
| 49 | 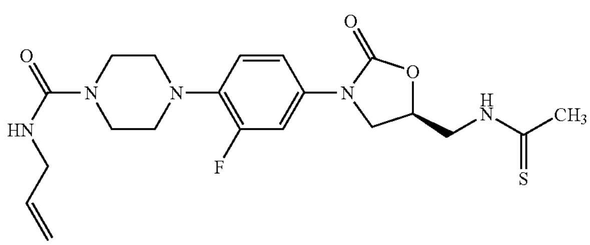 | ¹H-NMR (CDCl₃): δ 2.5(3H, s), 3.0(4H, t), 3.5(4H, t), 3.8(1H, t) 3.9(1H, t), 4.0(2H, t), 4.1(1H, d), 4.2(1H, s), 4.9(1H, d), 5.1(2H, m), 5.9(1H, s), 6.9–7.4(3H, m aromatic) Mass: M + 1 = 436 |

EXAMPLE 50

Synthesis of (S)-N-[3-[3-fluoro-4-[4-(morpholin-4-ylcarbonyl)piperazin-1-yl]phenyl]-2-oxooxazolidin-5-ylmethyl]acetamide

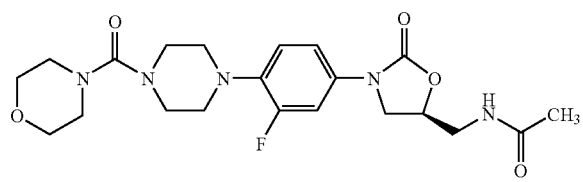

(S)-N-[3-[3-Fluoro-4-[piperazin-1-yl]phenyl]-2-oxooxazolidin-5-ylmethyl]acetamide (154 mg, 0.4587 mmol) was treated with morphonylcarbonylchloride (82 mg, 0.5504 mmol) and anhydrous potassium carbonate (190 mg, 1.376 mmol) in dimethylformamide (10 ml). The reaction mixture was allowed to react at 30° C. for 8 hrs, after which the reaction mixture was extracted with ethylacetate and water. The organic phase was separated and evaporated under reduced pressure to afford crude product. The crude was purified by column chromatography using silica gel using ethylacetate and methanol (9:1) as the eluent to afford pure title compound as colourless solid (85 mg).

¹H-NMR (CDCl₃): δ 2.0 (3H, s), 3.0 (4H, m), 3.3 (4H, m), 3.4 (4H, m), 3.6 (1H, m), 3.7 (6H, m), 4.02 (1H, m), 4.9 (1H, m), 6.8–7.4 (3H, m aromatic). Mass: M+1=450.

The following compounds were prepared according to the procedure given in example 50.

| Example No. | Structure | Analytical Data |
|---|---|---|
| 51 | (morpholine-C(O)-piperazine-fluorophenyl-oxazolidinone-CH2-NH-C(S)-CH3) | $^1$H-NMR (CDCl$_3$): δ 2.6(3H, s), 3.1(1H, s), 3.0(4H, m), 3.26(4H, m), 3.3(4H, m), 3.67(4H, m), 4.01(1H, m), 4.08(2H, m), 4.28(1H, m), 4.96(1H, m), 6.9–7.4(3H, m aromatic). Mass: M + 1 = 466 |

Antimicrobial Testing

The compounds of invention showed in vitro antibacterial activity when tested by the Agar Dilution Method as specified in documents published by the National Committee for Clinical Laboratory Standards (NCCLS), USA.

Briefly, the compounds of invention were weighed, dissolved in Dimethyl Sulfoxide, serially diluted in the same solvent and then incorporated into molten Mueller Hinton Agar in a petridish before solidification, with each petridish containing a different concentration of a compound.

The Bacterial Inoculum was prepared by touching the tops of 3 to 5 well isolated bacterial colonies with the same morphological appearance from an 18 hour old culture with an inoculating loop, transfering the growth to a tube containing 5 ml of normal saline and adjusting the turbidity of the saline suspension to 0.5 Macfarland Turbidity Standard equivalent to a bacterial population of $1.5 \times 10^8$ colony forming units (CFU) per millilitre of suspension.

The bacterial inoculum prepared in the above manner was inoculated onto petri dishes containing Mueller Hinton Agar which had earlier been incorporated with different dilutions of the compounds of invention by a Multipoint Inoculator with each inoculum spot containing approximately $1 \times 10^4$ colony forming units (CFU) of bacteria.

The inoculated petridishes were incubated at 35° Celsius in an ambient atmosphere for 20 hours. Petridishes containing different concentrations of Vancomycin and Oxacillin and inoculated with *Staphylococcus aureus*, Coagulase Negative *Staphylococci* and *Enterococci* were incubated for 24 hours.

The petridishes after incubation, were placed on a dark non reflecting surface and the Minimum Inhibitory Concentration (MIC) recorded as the concentration which showed no growth of the inoculated culture.

The following minimum inhibitory concentrations (μg/ml) were obtained for representative compounds of the invention which are given in the following table:

Minimum Inhibitory Concentration (MIC in μg/ml)

| Organism | 1 | 3 | 5 | 6 | 7 | 8 | 13 | 14 | 22 | 45 | 46 | 47 |
|---|---|---|---|---|---|---|---|---|---|---|---|---|
| *S. aureus* MRO 00013 | 0.5 | 1.0 | 0.5 | 1.0 | 1.0 | 0.5 | 1.0 | 0.5 | 1 | 0.5 | 0.5 | 0.5 |
| *S. aureus* MRO 00055 | 0.5 | 1.0 | 0.5 | 1.0 | 0.5 | 0.5 | 1.0 | 0.5 | 1 | 0.5 | 0.5 | 0.5 |
| *S. epidermidis* MRO 02046 | 0.25 | 0.5 | 0.25 | 0.25 | 0.25 | 0.25 | 0.25 | 0.25 | <0.25 | 0.25 | 0.25 | 0.25 |
| *S. aureus* MRO 00001 | 0.25 | 0.5 | 0.5 | 0.25 | 0.25 | 0.25 | 0.25 | 0.25 | 0.5 | 0.25 | 0.25 | 0.25 |
| *S. aureus* MRO 00003 | 0.5 | 1.0 | 0.5 | 1.0 | 0.5 | 0.5 | 1.0 | 0.5 | 0.5 | 0.5 | 0.5 | 0.5 |
| *S. aureus* MRO 00030 | 0.5 | 0.5 | 0.5 | 0.5 | 0.5 | 0.5 | 0.5 | 0.5 | 0.5 | 0.5 | 0.5 | 0.5 |
| *S. aureus* MRO 00048 | 0.25 | 0.25 | 0.25 | 0.25 | 0.5 | 0.25 | 0.25 | 0.25 | <0.25 | 0.25 | 0.25 | 0.25 |
| *S. aureus* MRO 00059 | 0.5 | 0.25 | 0.5 | 0.25 | 0.5 | 0.25 | 0.5 | 0.25 | 0.5 | 0.5 | 0.5 | 0.25 |
| *E. fecalis* MRO 04045 | 0.5 | 1.0 | 1.0 | 1.0 | 0.5 | 0.25 | 1.0 | 0.25 | 1 | 0.25 | 0.25 | 0.25 |
| *E. faecalis* ATCC 51299 | 0.50 | 0.25 | 0.5 | 0.25 | 0.5 | 0.25 | 0.5 | 0.25 | <0.25 | 0.25 | 0.25 | 0.25 |
| *E. faecalis* ATCC 29212 | 0.5 | 0.5 | 0.5 | 0.5 | 0.5 | 0.25 | 0.5 | 0.25 | 0.5 | 0.25 | 0.25 | 0.25 |
| *S. aureus* ATCC 29213 | 0.25 | 0.5 | 0.5 | 0.5 | 0.5 | 0.5 | 0.25 | 0.5 | 0.5 | 0.5 | 0.5 | 0.5 |
| *S. aureus* ATCC 43300 | 0.25 | 0.25 | 0.25 | 0.25 | 0.5 | 0.25 | 0.5 | 0.25 | 0.5 | 0.25 | 0.25 | 0.25 |
| *M. catarrhalis* ATCC 43627 | 1.0 | 1.0 | 1.0 | 1.0 | 2 | 2.0 | 2.0 | 2.0 | 1 | — | 2 | — |
| *M. catarrhalis* ATCC 43617 | 1.0 | 1.0 | 0.5 | 1.0 | 2 | 2.0 | 2.0 | 2.0 | 1 | — | 2 | — |
| *M. catarrhalis* ATCC 43628 | 1.0 | 1.0 | 0.5 | 1.0 | 2 | 2.0 | 2.0 | 2.0 | 1 | — | 2 | — |

1). *S. aureus*—Staphylococus aureus
2). *Ent. Faecalis*—Enterococcus faecalis
3). *E. faecium*—Enterococcus faecium
4). *M. catarrhalis*—Morexella catarrhalis
5). ATCC—American Type Culture Collection
6). MRO—Microbial Resource Orchid.

The invention claimed is:
1. A compound represented by formula (I):

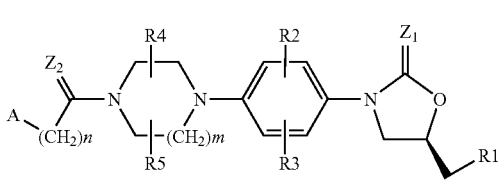

their derivatives, their analogs, their tautomeric forms, their stereoisomers, their polymorphs, and their pharmaceutically acceptable salts, wherein:
$Z^1$ represents O or S;
$Z^2$ represents S;
$R^1$ represents a substituent selected from the group consisting of:
  a halogen group,
  an azido group,
  a nitro group,
  a cyano group,
  $XR^6$, where:
    X represents O or S; and
    $R^6$ represents a substituent selected from the group consisting of:
      hydrogen,
      formyl, and
      a substituted or unsubstituted group selected from the group consisting of ($C_1$–$C_6$)alkyl, cycloalkyl, aryl, aralkyl, acyl, thioacyl, heterocyclyl, heteroaryl, alkylsulfonyl, arylsulfonyl, and aralkylsulfonyl;
  $N(R^{7a}R^{7b})$ where:
    $R^{7a}$ and $R^{7b}$ each independently represent a substituent selected from the group consisting of:
      hydrogen,
      a formyl group,
      a substituted or unsubstituted group selected from the group consisting of($C_1$–$C_6$)alkyl, aryl, aralkyl, heteroaryl, heteroaralkyl, and an aminoacid residue which is attached through an acid moiety, or
    $R^{7a}$ and $R^{7b}$ together with nitrogen represents a mono or bicyclic saturated or unsaturated ring system which may contain one or more heteroatoms selected from O, S or N;
  a formula —NHC(=Y)$R^8$ wherein:
    Y represents O or S; and
    $R^8$ is a hydrogen atom or a substituted or unsubstituted substituent selected from the group consisting of a ($C_1$–$C_6$)alkyl group, a ($C_1$–$C_6$)alkoxy group, an aryl group, a ($C_3$–$C_6$)cycloalkyl group, an amino group, a monoalkylamino group, a dialkylamino group, a cycloalkylamino group, an arylamino group, an aroylamino group, an alkylcarbonylamino group, an arylcarbonylamino group, a heteroaryl group, a heterocyclyl group, a heteroaralkyl group, and a heteroaroylamino group; and
  a formula selected from the group consisting of:
    —NHS(O)$_p$($C_1$–$C_4$)alkyl,
    —NHS(O)$_p$($C_1$–$C_4$)aryl, and
    —NHS(O)$_p$($C_1$–$C_4$)heteroaryl,
    where p is 0 to 2;

$R_2$ and $R_3$ are the same or different and independently represent a hydrogen, a halogen, a hydroxy group, an alkyl group, or an alkoxy group;
$R_4$ and $R_5$ are the same or different and independently represent a hydrogen, a cyano group, a nitro group, an amino group, a halogen, a hydroxyl group, or a substituted or unsubstituted group selected from the group consisting of ($C_1$–$C_6$)alkyl, haloalkyl, ($C_1$–$C_6$)alkoxy, ($C_1$–$C_6$)alkylthio, ($C_3$–$C_6$)cycloalkyl, or either of $R^4$ or $R^5$ represent an oxo or thiooxo group;
n is 0, 1,or2;
A represents a substituent selected from the group consisting of:
  a substituted or unsubstituted five-membered heteroaryl group having at least one nitrogen atom,
  a substituted or unsubstituted five-membered heterocyclyl group having at least one nitrogen atom, wherein the heterocycle group is attached through a carbon atom,
  a substituted or unsubstituted five-membered heteroarylalkenyl group having at least one nitrogen atom, and
  a substituted or unsubstituted five-membered heterocyclylalkenyl group having at least one nitrogen atom;
m is an integer in the range of 0 to 2; and
n is an integer ranging from 0 to 4.

2. The compound according to claim 1, wherein:
A represents a substituted or unsubstituted substituent selected from the group consisting of pyrrolyl, oxazolyl, thiazolyl, imidazolyl, isooxazolyl, oxadiazolyl, triazolyl, thiadiazolyl, tetrazolyl, pyrrolidinyl, a five-membered heteroaryl alkenyl containing at least one nitrogen member, and a five-membered heterocyclyl alkenyl containing at least one nitrogen member.

3. The compound according to claim 1, wherein formula (I) represents:
  (S)-N-[3-[3-Fluoro-4-[4-(5-nitrofuran-2-ylthiocarbonyl)piperazin-1-yl]phenyl]-2-oxooxazolidin-5-ylmethyl]thioacetamide;
  (S)-N-[3-[3-Fluoro-4-[4-(3-methylisoxazol-5-ylthiocarbonyl)piperazin-1-yl]phenyl]-2-oxooxazolidin-5-ylmethyl]thioacetamide;
  (S)-N-[3-[3-Fluoro-4-[4-(5-methylisoxazol-3-ylthiocarbonyl)piperazin-1-yl]phenyl]-2-oxooxazolidin-5-ylmethyl]thioacetamide;
  (S)-N-[3-[3-Fluoro-4-[4-(imidazol-2-ylthiocarbonyl)piperazin-1-yl]phenyl]-2-oxooxazolidin-5-ylmethyl]thioacetamide;
  (S)-N-[3-[3-Fluoro-4-[4-(pyrrolidin-2-ylthiocarbonyl)piperazin-1-yl]phenyl]-2-oxooxazolidin-5-ylmethyl]acetamide;
  (S)-N-[3-[3-Fluoro-4-[4-(pyrrolidin-2-ylthiocarbonyl)piperazin-1-yl]phenyl]-2-oxooxazolidin-5-ylmethyl]thioacetamide;
  (S)-N-[3-[3-Fluoro-4-[4-(5-nitrofuran-3-ylthiocarbonyl)piperazin-1-yl]phenyl]-2-oxooxazolidin-5-ylmethyl]acetamide;
  (S)-N-[3-[3-Fluoro-4-[4-(imidazol-2-ylthiocarbonyl)piperazin-1-yl]phenyl]-2-oxooxazolidin-5-ylmethyl]acetamide;
  (S)-N-[3-[3-Fluoro-4-[4-(5-methyl-i ,2,4-triazoly-3-ylthiocarbonyl)piperazin-1-yl]phenyl]-2-oxooxazolidin-5-ylmethyl]thioacetamide;
  (S)-N-[3-[3-Fluoro-4-[4-(5-methyl-i ,2,4-triazoiy-3-ylthiocarbonyl)piperazin-1-yl]phenyl]-2-oxooxazolidin-5-ylmethyl]acetamide;
  (S)-N-[3-[3-Fluoro-4-[4-(5-ethyl-i ,2,4-triazoly-3-ylthiocarbonyl)piperazin-1-yl]phenyl]-2-oxooxazolidin-5-ylmethyl]thioacetamide;

(S)-N-[3-[3-Fluoro-4-[4-(5-ethyl-1,2,4-triazoly-3-ylthiocarbonyl)piperazin-1-yl]phenyl]-2-oxooxazolidin-5-ylmethyl]acetamide;

(S)-N-[3-[3-Fluoro-4-[4-(1,3,4-oxadiazol-2-ylthiocarbonyl)piperazin-1-yl]phenyl]-2-oxooxazolidin-5-ylmethyl]thioacetamide;

(S)-N-[3-[3-Fluoro-4-[4-(1,3,4-oxadiazol-2-ylthiocarbonyl)piperazin-1-yl]phenyl]-2-oxooxazolidin-5-ylmethyl]acetamide;

(S)-N-[3-[3-Fluoro-4-[4-(5-methyl-1,3,4-oxadiazol-2-ylthiocarbonyl)piperazin-1-yl]phenyl]-2-oxooxazolidin-5-ylmethyl]thioacetamide;

(S)-N-[3-[3-Fluoro-4-[4-(5-methyl-1,3,4-oxadiazol-2-ylthiocarbonyl)piperazin-1-yl]phenyl]-2-oxooxazolidin-5-ylmethyl]acetamide;

(S)-N-[3-[3-Fluoro-4-[4-(1,3,4-thiadiazol-2-ylthiocarbonyl)piperazin-1-yl]phenyl]-2-oxooxazolidin-5-ylmethyl]thioacetamide;

(S)-N-[3-[3-Fluoro-4-[4-(1,3,4-thiadiazol-2-ylthiocarbonyl)piperazin-1-yl]phenyl]-2-oxooxazolidin-5-ylmethyl]acetamide;

(S)-N-[3-[3-Fluoro-4-[4-(1,3,4-oxadiazol-2-ylthioacetyl)piperazin-1-yl]phenyl]-2-oxooxazolidin-5-ylmethyl]thioacetamide;

(S)-N-[3-[3-Fluoro-4-[4-(1,3,4-oxadiazol-2-ylthioacetyl)piperazin-1-yl]phenyl]-2-oxooxazolidin-5-ylmethyl]acetamide;

(S)-N-[3-[3-Fluoro-4-[4-(5-methylimidazol-2-ylthiocarbonyl)piperazin-1-yl]phenyl]-2-oxooxazolidin-5-ylmethyl]thioacetamide;

(S)-N-[3-[3-Fluoro-4-[4-(5-methylimidazol-2-ylthiocarbonyl)piperazin-1-yl]phenyl]-2-oxooxazolidin-5-ylmethyl]acetamide;

(S)-N-[3-[3-Fluoro-4-[4-(1,2,4-triazol-3-ylthiocarbonyacetyl)piperazin-1-yl]phenyl]-2-oxooxazolidin-5-ylmethyl]thioacetamide;

(S)-N-[3-[3-Fluoro-4-[4-(1,2,4-triazol-3-ylthiocarbonyacetyl)piperazin-1-yl]phenyl]-2-oxooxazolidin-5-ylmethyl]acetamide;

(S)-N-[3-[3-Fluoro-4-[4-(5-methyl-1,3,4-thiadiazol-2-ylthiocarbonyl)piperazin-1-yl]phenyl]-2-oxooxazolidin-5-ylmethyl]acetamide;

(S)-N-[3-[3-Fluoro-4-[4-(5-methyl-1,3,4-thiadiazol-2-ylthiocarbonyl)piperazin-1-yl]phenyl]-2-oxooxazolidin-5-ylmethyl]thioacetamide;

(S)-N-[3-[3-Fluoro-4-[4-(5-methyloxazol-2-ylthiocarbonyl)piperazin-1-yl]phenyl]-2-oxooxazolidin-5-ylmethyl]thioacetamide;

(S)-N-[3-[3-Fluoro-4-[4-(5-methyloxazol-2-ylthiocarbonyl)piperazin-1-yl]phenyl]-2-oxooxazolidin-5-ylmethyl]acetamide;

(S)-N-[3-[3-Fluoro-4-[4-(oxazol-2-ylthiocarbonyl)piperazin-1-yl]phenyl]-2-oxooxazolidin-5-ylmethyl]thioacetamide;

(S)-N-[3-[3-Fluoro-4-[4-(oxazol-2-ylthiocarbonyl)piperazin-1-yl]phenyl]-2-oxooxazolidin-5-ylmethyl]acetamide;

(S)-N-[3-[3-Fluoro-4-[4-(2-methyloxazol-5-ylthiocarbonyl)piperazin-1-yl]phenyl]-2-oxooxazolidin-5-ylmethyl]thioacetamide;

(S)-N-[3-[3-Fluoro-4-[4-(2-methyloxazol-5-ylthiocarbonyl)piperazin-1-yl]phenyl]-2-oxooxazolidin-5-ylmethyl]acetamide;

(S)-N-[3-[3-Fluoro-4-[4-(oxazol-5-ylthiocarbonyl)piperazin-1-yl]phenyl]-2-oxooxazolidin-5-ylmethyl]acetamide; and (S)-N-[3-[3-Fluoro-4-[4-(oxazol-5-ylthiocarbonyl)piperazin-1-yl]phenyl]-2-oxooxazolidin-5-ylmethyl]thioacetamide.

4. The compound according to claim 3, wherein the salt is selected from hydrochloride or hydrobromide.

5. A process for making the compound according to claim 1, comprising:

i) deprotecting the compound of the formula (IIIa)

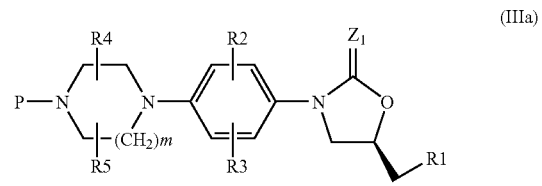

(IIIa)

where P represents a protecting group to produce compound of formula (IIIb)

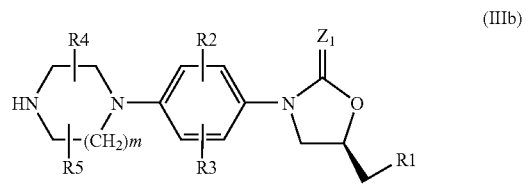

(IIIb)

ii) reacting the compound of formula (IIIb) with a compound of formula (IIIc)

(IIIc)

where $L_1$ is a leaving group.

6. A process for making the compound according to claim 1, wherein $R^1$ represents —NHC(=Y)$R^8$ wherein:

Y represents O or S; and $R^8$ is a hydrogen atom or a substituted or unsubstituted substituent selected from the group consisting of a $(C_1-C_6)$alkyl group, a $(C_1-C_6)$alkoxy group, an aryl group, a $(C_3-C_6)$cycloalkyl group, an amino group, a monoalkylamino group, a dialkylamino group, a cycloalkylamino group, an arylamino group, an aroylamino group, an alkylcarbonylamino group, an arylcarbonylamino group, a heteroaryl group, a heterocyclyl group, a heteroaralkyl group, and a heteroaroylamino group, comprising:

a) reacting a compound represented by the formula (IIId)

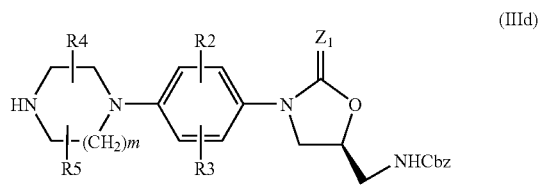

(IIId)

where $L_1$ is a leaving group, with a compound represented by formula (IIIe)

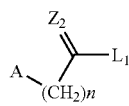
(IIIe)

to produce a compound represented by formula (IIIf):

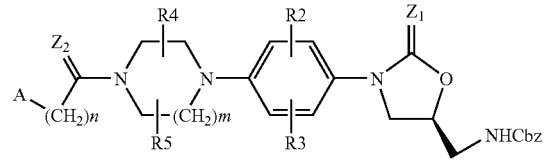
(IIIf)

b) reducing the product of step (a) represented by formula (IIIf) to produce a compound represented by formula (IIIg):

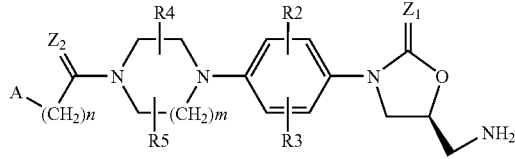
(IIIg)

and c) acylating the product of step (b) represented by formula (IIIg) to produce a compound represented by formula (I).

7. A process for making the compound according to claim 1, wherein $R^1$ represents a substituent selected from the group consisting of:
a halogen group,
an azido group,
a nitro group,
a cyano group,
$XR^6$, where:
  X represents O or S; and
  $R^6$ represents a substituent selected from the group consisting of:
    hydrogen,
    formyl, and
    a substituted or unsubstituted group selected from the group consisting of $(C_1–C_6)$alkyl, cycloalkyl, aryl, aralkyl, acyl, thioacyl, heterocyclyl, heteroaryl, alkylsulfonyl, arylsulfonyl, and aralkylsulfonyl;
$N(R^{7a}R^{7b})$ where:
  $R^{7a}$ and $R^{7b}$ each independently represent a substituent selected from the group consisting of:
    hydrogen,
    a formyl group,
    a substituted or unsubstituted group selected from the group consisting of $(C_1–C_6)$alkyl, aryl, aralkyl, heteroaryl, heteroaralkyl, and an aminoacid residue which is attached through an acid moiety, or $R^{7a}$ and $R^{7b}$ together with nitrogen represents a mono or bicyclic saturated or unsaturated ring system which may contain one or more heteroatoms selected from O, S or N, comprising:
  reacting a compound represented by formula (IIIh)

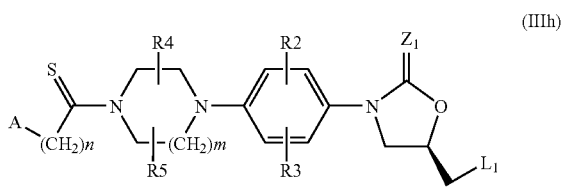
(IIIh)

where $L^1$ represents a leaving group of mesylate, tosylate, or triflate with $R^6XH$ or $NH(R^{7a}R^{7b})$.

8. A process for making the compound according to claim 1, wherein $R^1$ represents a $—NHS(O)_r(C_1–C_4)$alkyl group, a $—NHS(O)_r$aralkyl group, or a $—NHS(O)_r$ heteroaralkyl group, comprising:

reacting a compound represented by formula (IIIg):

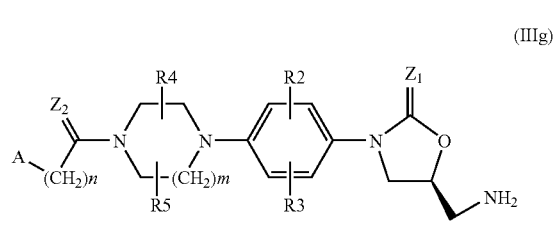
(IIIg)

with $R'SO_2Cl$, where R' represents a $(C_1–C_4)$alkyl group, an aralkyl group, or a heteroaralkyl group.

9. A process for making the compound according to claim 1, wherein $R^1$ represents $—NHC(\!\!=\!\!Y)R^8$ wherein:
  Y represents O or S; and
  $R^8$ is a hydrogen atom or a substituted or unsubstituted substituent selected from the group consisting of a $(C_1–C_6)$alkyl group, a $(C_1–C_6)$alkoxy group, an aryl group, a $(C_3–C_6)$cycloalkyl group, an amino group, a monoalkylamino group, a dialkylamino group, a cycloalkylamino group, an arylamino group, an aroylamino group, an alkylcarbonylamino group, an arylcarbonylamino group, a heteroaryl group, a heterocyclyl group, a heteroaralkyl group, and a heteroaroylamino group, comprising:
  i) reacting a compound represented by formula (IIIi):

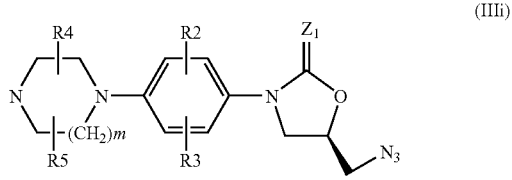
(IIIi)

with a compound represented by formula (IIIb):

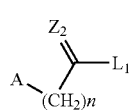
(IIIb)

where L₁ is as leaving group, to produce a compound represented by formula (IIIj):

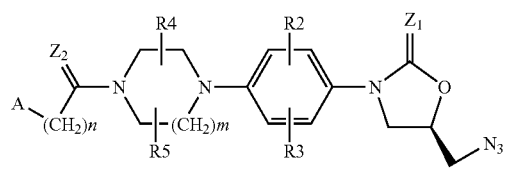
(IIIj)

and b) acylating the product of step (a) represented by formula (IIIj) to produce a compound represented by formula (I).

10. A process for making the compound according to claim 1, wherein $R^1$ represents —NHC(=Y)$R^8$ wherein:

Y represents O or S; and $R^8$ is a hydrogen atom or a substituted or unsubstituted substituent selected from the group consisting of a $(C_1-C_6)$alkyl group, a $(C_1-C_6)$alkoxy group, an aryl group, a $(C_3-C_6)$cycloalkyl group, an amino group, a monoalkylamino group, a dialkylamino group, a cycloalkylamino group, an arylamino group, an aroylamino group, an alkylcarbonylamino group, an arylcarbonylamino group, a heteroaryl group, a heterocyclyl group, a heteroaralkyl group, and a heteroaroylamino group, comprising:

i) reacting a compound represented by formula (IIIa):

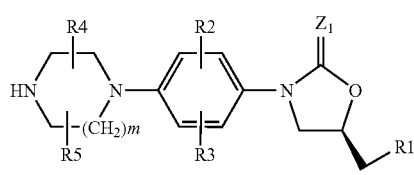
(IIIa)

wherein $R^1$ represents —NHC(=Y)$R_8$ where Y is O or S, with a compound represented by formula (IIIk):

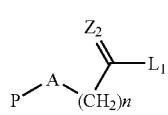
(IIIk)

wherein P represents a protecting group to yield a compound represented by formula (IIIl):

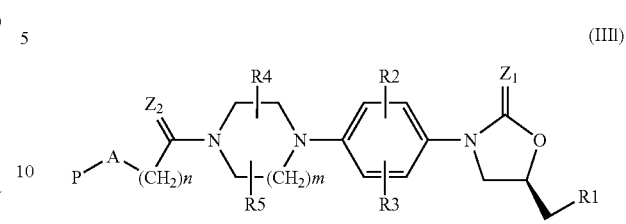
(IIIl)

wherein $R^1$ represents —NHC(=Y)$R^8$ where Y is O or S, and ii) deprotecting the product of step (i) represented by formula (IIIl) to produce a compound represented by formula (I).

11. A process for making the compound according to claim 1, wherein $R^1$ represents —NHC(=Y)$R^8$ wherein:

Y represents O or S; and $R^8$ is a hydrogen atom or a substituted or unsubstituted substituent selected from the group consisting of a $(C_1-C_6)$alkyl group, a $(C_1-C_6)$alkoxy group, an aryl group, a $(C_3-C_6)$cycloalkyl group, an amino group, a monoalkylamino group, a dialkylamino group, a cycloalkylamino group, an arylamino group, an aroylamino group, an alkylcarbonylamino group, an arylcarbonylamino group, a heteroaryl group, a heterocyclyl group, a heteroaralkyl group, and a heteroaroylamino group, comprising:

i) reacting a compound represented by formula (IIIi):

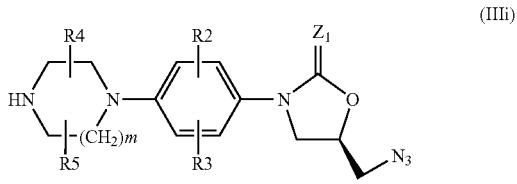
(IIIi)

wherein $R^1$ represents —NHC(=Y)$R^8$ where Y is O or S, with a compound represented by formula (IIIk):

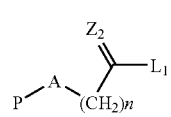
(IIIk)

wherein P represents a protecting group, to yield a compound represented by formula (IIIm):

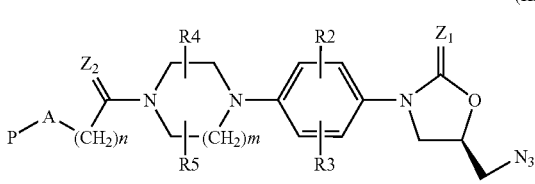
(IIIm)

ii) acylating the product of step (i) represented by formula (IIIm) to produce a compound represented by formula (IIIl):

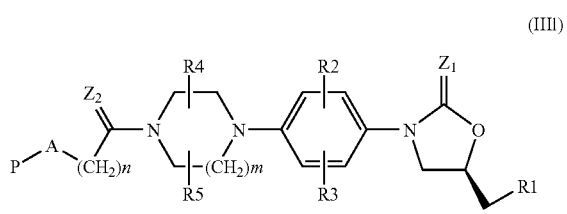

(IIIl)

wherein R$^1$ represents —NHC(=Y)R$^8$, and iii) deprotecting the product of step (ii) represented by formula (IIIl) to produce a compound represented by formula (I).

12. A process for making the compound according to claim 1, wherein any of the groups Y and Z$^2$ represent O to compounds where Y and Z$^2$ represent S using Lawesson's reagent.

13. A pharmaceutical composition, comprising a compound according to claim 1, and a pharmaceutically acceptable carrier, diluent, excipient, or solvate.

14. A pharmaceutical composition according to claim 13, wherein the composition is in the form of a tablet, capsule, powder, syrup, solution, aerosol, or suspension.

15. A method of treating a bacterial infectious disorder in a human or animal, comprising administering an effective amount of a compound according to claim 1 to said human or animal in need thereof.

16. A method of treating a bacterial infectious disorder in a human or animal, comprising administering an effective amount of a compound according to claim 3 to said human or animal in need thereof.

17. A method of treating a bacterial infectious disorder in a human or animal, comprising administering the composition according to claim 13 to said human or animal in need thereof.

* * * * *